United States Patent
Tao et al.

(10) Patent No.: US 7,759,490 B2
(45) Date of Patent: Jul. 20, 2010

(54) PHOSPHORESCENT OSMIUM (II) COMPLEXES AND USES THEREOF

(75) Inventors: Ye Tao, Ottawa (CA); Yun Chi, Hsinchu (TW); Yung-Liang Tung, Hualien (TW); Arthur Carty, Ottawa (CA); Pi-Tai Chou, Taipei (TW)

(73) Assignees: National Research Council of Canada, Ottawa (CA); National Tsing Hua University, Hsinchu (TW)

( * ) Notice: Subject to any disclaimer, the term of this patent is extended or adjusted under 35 U.S.C. 154(b) by 0 days.

(21) Appl. No.: 12/216,833

(22) Filed: Jul. 11, 2008

(65) Prior Publication Data

US 2009/0058281 A1  Mar. 5, 2009

(30) Foreign Application Priority Data

Nov. 7, 2003 (CA) .................................... 2448718

(51) Int. Cl.
C07F 15/00 (2006.01)
B32B 9/00 (2006.01)
(52) U.S. Cl. .............................. 546/2; 428/690; 546/10; 544/225
(58) Field of Classification Search .................... 546/2, 546/10; 544/225; 428/690
See application file for complete search history.

(56) References Cited

U.S. PATENT DOCUMENTS 6,911,677 B2  6/2005  Igarashi

OTHER PUBLICATIONS

Baldo, M.A. et al., Highly efficient phosphorescent emission from organic electroluminescent devices, Nature, vol. 395, Sep. 1998, p. 151.
Carlson, Brenden et al., Divalent Osmium Complexes: Synthesis, Characterization, Strong Red Phosphorescence, . . . , J.Am. Soc. 2002, 124, pp. 14162-14174.
Lamansky, Sergey et al., Highly Phosphorescent Bis-Cyclometalated Iridium Complexes: Synthesis, . . . J. Am. Chem. Soc. 2001, 123, pp. 4304-4312.
Brooks, Jason, Synthesis and Characterization of Phosphorescent Cyclometalated Platinum Complexes, Inroganic Chemistry, vol. 41, No. 12, 2002, pp. 3055-3066.
Tung, Yung-Liang, Highly Efficient Red Phosphorescent Osmium(II) Complexes for OLED Applications, Organometallics 2004, vol. 23, No. 15, 2004, pp. 3745-3748.
Wu,P. et al.: Synthesis and charaterization of metal complexes possessing the 5-(2-pyridyl) pyrazolate ligands. Organometallics, vol. 22, pp. 4938-4946,2003.

*Primary Examiner*—Charanjit S Aulakh
(74) *Attorney, Agent, or Firm*—Shlesinger, Arkwright & Garvey LLP

(57) ABSTRACT

There is disclosed herein phosphorescent compounds, uses thereof, and devices including organic light emitting diode (OLEDs) including such compounds.

Compounds of interest include:

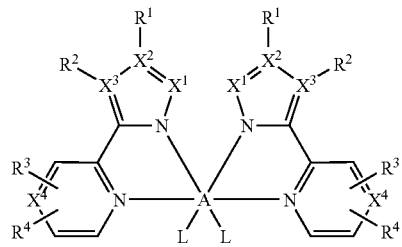

wherein A is Os or Ru

The anionic chelating chromophores N^N, which are formed by connecting one pentagonal ring structure containing at least two nitrogen atoms to a hexagonal pyridine type of fragment via a direct carbon-carbon linkage.

L is a neutral donor ligand; the typical example includes carbonyl, pyridine, phosphine, arsine and isocyanide; two neutral L's can also combine to produce the so-called chelating ligand such as 2,2'-bipyridine, 1,10-phenanthroline and N-heterocyclic carbene (NHC) ligand, or bidentate phosphorous ligands such as 1,2-bis(diphenylphosphino)ethane, 1,2-bis(diphenylphosphino)benzene.

L can occupy either cis or trans orientation.

When L occupies the trans position, the preferred structure contains both the hexagonal fragment of N^N as well as its pentagonal fragment located at the trans position respect to their counterparts of the second N^N chromophore.

When L occupies the cis position, the preferred structure consists of the pentagonal unit of N^N chromophores residing opposite to the L.

$X^1$, $X^2$ and $X^3$ independently are C or N;
when $X^2$ is N, $R^1$ is omitted,
when $X^3$ is N, $R^2$ is omitted,
$R^1$ is H, C1-C8 alkyl, C1-C8 substituted phenyl or C1-C4 perfluoroalkyl,
$R^2$ is H, F or cyano substituent,
$X^4$ is either C or N;
$X^4$ may locate at any position of the hexagonal ring, when $X^4$ is N and $R^3$ and $R^4$ are not linked to $X^4$,
$R^3$ is H, methyl or C1-C3 small alkyl, $R^4$ is H, methyl or C1-C3 small alkyl, or $R^3$ and $R^4$ together form an additional conjugated unit with structure

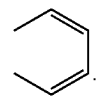

32 Claims, 9 Drawing Sheets Figure 3 (prior art):
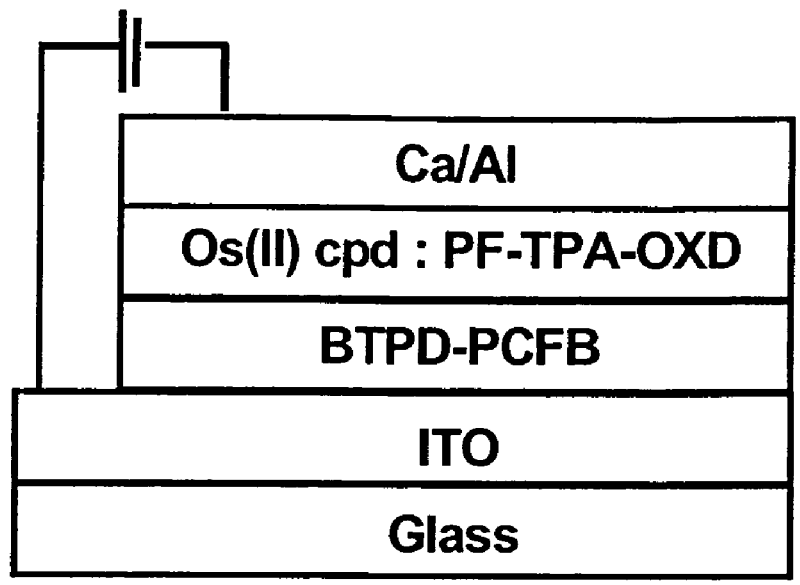
Figure 4: The first example.
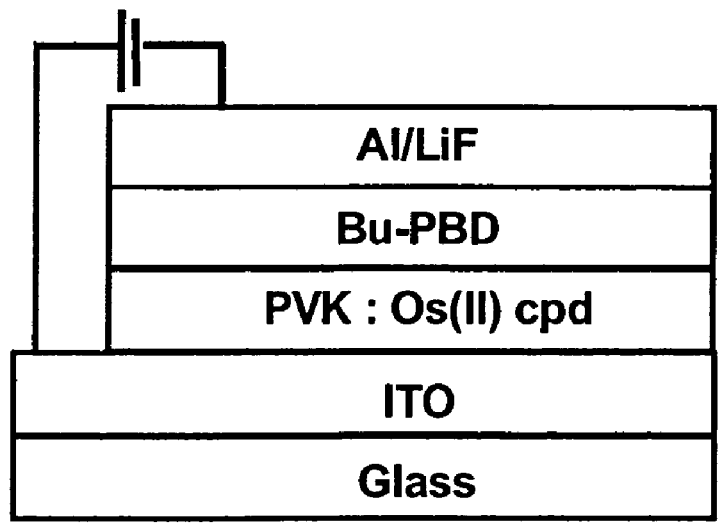

Figure 6. The basic structural motif of an embodiment of OLED devices.
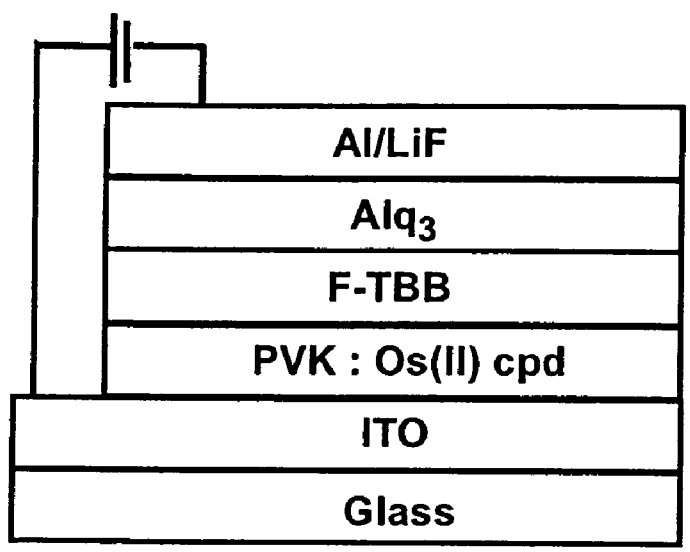

ORTEP diagram of Os1; selected distances: Os-P(1) = 2.3616(5), Os-N(1) = 2.090(2), Os-N(2) = 2.073(2), N(2)-N(3) = 1.349(2), N(2)-C(6) = 1.352(3), N(3)-C(8) = 1.355(3) Å and angles: N(1)-Os-N(2) = 76.48(7), N(1)-Os-N(2A) = 103.52(7)°.

Figure 11 UV-vis absorption and normalized PL emission spectra of Os1 (squares), Os2 (triangles), and Os3 (circles) in $CH_2Cl_2$ at room temperature.
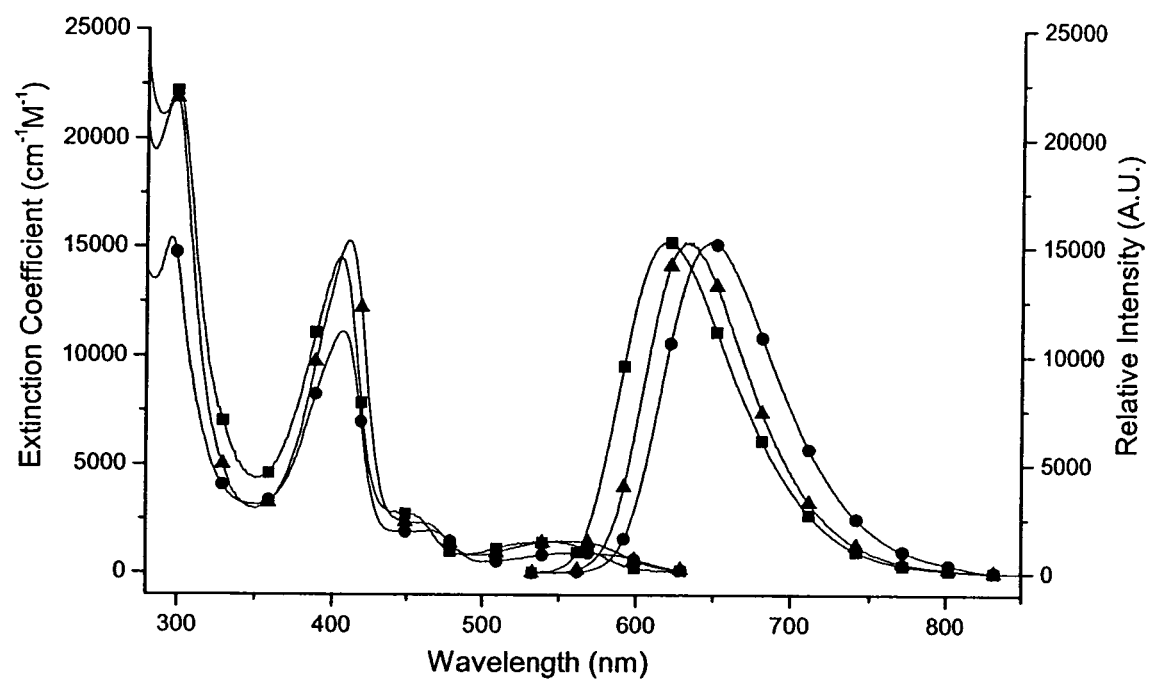

PHOSPHORESCENT OSMIUM (II) COMPLEXES AND USES THEREOF

CROSS-REFERENCE TO RELATED APPLICATIONS

This application is a continuation of U.S. Ser. No. 10/981,755 filed on Nov. 5, 2004 which is incorporated herein by reference.

FIELD OF THE INVENTION

The invention relates to phosphorescent compounds and uses thereof.

BACKGROUND

It has long been felt that a technically viable emissive display technology could compete with the currently dominating technology of liquid crystal displays (LCDs), and OLEDs are presently considered well placed to do so. While the technology of LCDs has various limitations such as low efficiency, poor viewing angles, slow switching speed and narrow temperature ranges, the main advantages of OLEDs are full color, high efficiency, large viewing angles, high switching speed, and low operational temperature. Therefore, organic light emitting diodes (OLEDs) and polymer light emitting diodes (PLEDs) have attracted a tremendous amount of research interests from both academia and industry in the past decade. New light emitting devices based on organic materials are researched and engineered for both display applications and general solid-state lighting. A lot of work is going on in chemistry laboratories to find materials with high luminous quantum efficiency, good color purity and great stability for the application to OLED displays. While some materials meet or exceed some of the requirements for commercial displays, none are believed to meet them all. Efficient and stable red and blue emitters are especially lacking.

Most organic or polymer light emitting diodes emit light through the radiative decay of singlet excitons. As the electron-hole recombination with uncorrelated spins has 75% probability to yield spin symmetric (S=1) state and 25% for spin asymmetric state (S=0), therefore the maximum internal quantum efficiency for the OLEDs and PLEDs using fluorescence as emission mechanism is capped at 25% (photon/electron). Any attempt to further enhance the internal efficiency has to resort to harvesting the triplet excitons in the devices [Baldo, M. A. et al., *Nature* 1998, 395, 151].

Organometallic complexes containing the third-row transition metal elements such as Os(II), Ir(III) and Pt(II) are crucial materials for this attempt. The strong spin-orbit coupling induced by these heavy metal ions promotes an efficient intersystem crossing from the singlet to the triplet state, which then facilitates high internal quantum efficiencies ($\eta_{int}$) for the OLED devices by using both singlet and triplet excitons. In this regard, numerous attempts have been made to exploit third-row transition metal complexes as dopant emitters for OLED fabrication, among which quite a few Pt(II) and Ir(III) metal complexes have been reported to exhibit highly efficient OLED and PLED device performances.

The design and synthesis of red emitting complexes is intrinsically difficult because their luminescence quantum yield tends to their ionic nature observed in the traditional design involving Os(II) complexes such as [Os(bpy)$_3$][PF$_6$]$_2$, where bpy=2,2'-bipyridine; [Carlson, B. et al., *J. Am. Chem. Soc.* 2002, 124, 14162]. The OLED devices prepared from [Os(bpy)$_3$][PF$_6$]$_2$ and the related derivatives suffered inferior performances compared with the neutral Pt(II) and Ir(III) counterparts; [(a) Lamansky, S. et al., *J. Am. Chem. Soc.* 2001, 123, 4304, and (b) Brooks, J. et al., *Inorg. Chem.* 2002, 41, 3055]. This is, in part, attributed to the lack of strong covalent bonding between the cationic Os(II) emitting complexes and their counter anions within the host matrix. The positively charged Os(II) fragments and their counter anions may undergo significant drifting under high electric field during device operation towards the cathode and the anode, respectively, leading to instability in device performance and a relatively long response time. Accordingly, it is proposed that only the utilization of neutral Os(II) emitting materials, can the goal of practical OLED applications be achieved. In this patent application, we propose the design and preparation of a new series of Os(II) emitting complexes, for which the ligand sphere of the OS(II) atom consists of two anionic chelating ligands such as 3-trifluoromethyl-5-(2-pyridyl) pyrazolate (fppz$^-$), 3-trifluoromethyl-5-(2-pyridyl) triazolate (bptz$^-$), or even (2-pyridyl) tetrazolate (pyN4$^-$) ligand that can neutralize and balance the 2+ charge located at the Os(II) center, and with two donor ligands such as carbonyl, pyridine, bipyridine, arsine, phosphine, and isocyanide ligands to complete the required octahedral coordination arrangement; [Tung, Y.-L. et al., *Organometallics* 2004, 23, 3745].

Thus, it is an object of the invention to provide Os(II) compound having phosphorescent properties, and uses thereof.

SUMMARY OF THE INVENTION

The invention provides octahedral Os (II) and Ru(II) complexes of structures I and II:

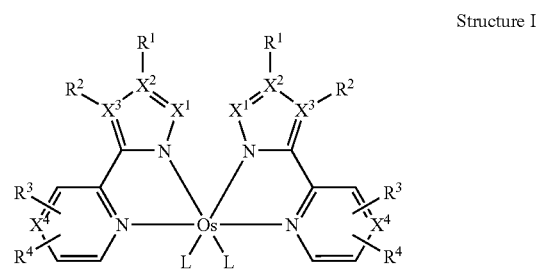

Structure I

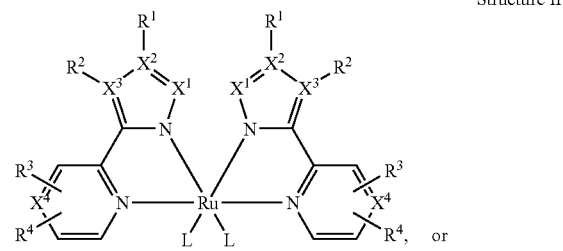

Structure II

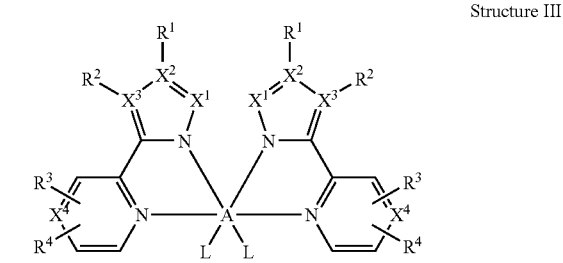

Structure III wherein A is Os or Ru

The anionic chelating chromophores N^N, which are formed by connecting one pentagonal ring structure containing at least two nitrogen atoms to a hexagonal pyridine type of fragment via a direct carbon-carbon linkage.

L stands for a neutral donor ligand; the typical example includes carbonyl, pyridine, phosphine, arsine and isocyanide; two neutral L's can also combine to produce the so-called chelating ligand such as 2,2'-bipyridine, 1,10-phenanthroline and N-heterocyclic carbene (NHC) ligand, or bidentate phosphorous ligands such as 1,2-bis(diphenylphosphino)ethane, 1,2-bis(diphenylphosphino)benzene.

L can occupy either cis or trans orientation.

When L occupies the trans position, the preferred structure contains both the hexagonal fragment of N^N as well as its pentagonal fragment located at the trans position respect to their counterparts of the second N^N chromophore.

When L occupies the cis position, the preferred structure consists of the pentagonal unit of N^N chromophores residing opposite to the L.

$X^1$, $X^2$ and $X^3$ independently are C or N;
when $X^2$ is N, $R^1$ is omitted,
when $X^3$ is N, $R^2$ is omitted,
$R^1$ is H, C1-C8 alkyl, C1-C8 substituted phenyl or C1-C4 perfluoroalkyl,
$R^2$ is H, F or cyano substituent,
$X^4$ is either C or N;
$X^4$ may locate at any position of the hexagonal ring, when $X^4$ is N and $R^3$ and $R^4$ are not linked to $X^4$,
$R^3$ is H, methyl or C1-C3 small alkyl, $R^4$ is H, methyl or C1-C3 small alkyl, or $R^3$ and $R^4$ together form an additional conjugated unit with structure

Also provided are OLEDs comprising compounds of structure I.

In an embodiment of the invention there is provided the synthesis of the above mentioned light-emitting Osmium(II) complexes described in structure I.

In an embodiment of the invention there is provided an Organic Light Emitting Diode (OLED), and A Polymer Light Emitting Diode (PLED), including as active material an Osmium(II) complexes described in structure I.

In an embodiment of the invention there is provided an Organic Light Emitting Diode (OLED), and A Polymer Light Emitting Diode (PLED), including as active material an Osmium(II) complexes described in structure I and with the possible ligands defined therein.

In an embodiment of the invention there is provided an Organic, Light Emitting Diode (OLED), and a Polymer Light Emitting Diode (PLED) as described above, wherein said Os(II) compound is mixed with a second active material. The second active material can be any other suitable electroluminescent material, (e.g. Alq3, derivatives of polyfluorene or oligofluorene, derivatives of polycarbazole or oligocarbazole, derivatives of poly(p-phenylenevinylene or oligo(phenylenevinylene), derivateis of poly(p-phenylene) or oligo(p-phenylene, and etc.). The second active material will in some instances emit at a different wavelength than the Os(II) compound. (e.g. Alq3, PPV and other polyfluorene derivatives, etc. The second active material can be an electron transport emitter, a hole transport emitter, or a bipolar emitter.

In an embodiment of the invention there is provided an OLED comprising a hole transport layer, an electron transport layer, and wherein at least one of said hole transport layer and said electron transport layer comprises either alone or in combination as active material such as Osmium(II) complexes described by structure I.

In an embodiment of the invention there is provided an OLED as described above, further comprising a carrier promotion layer, such as a hole injection layer (HIJL) or an electron injection layer (EIJL) adjacent at least one of said electron transport layer and said hole transport layer.

In an embodiment of the invention there is provided an OLED as described above, wherein said electron promotion is LiF.

In an embodiment of the invention there is provided an OLED as described above, wherein said hole promotion is [Poly (ethylene dioxythiophene: polystryrene sulfonate)] (PEDOT-PSS).

BRIEF DESCRIPTION OF THE DRAWINGS

FIG. 3 is a depiction of prior art ionic Os complex based phosphorescent dye doped polymer light-emitting diode.

FIG. 4 shows an embodiment of the invention where an OLED is formed using Os(II) complexes of formula (4) doped PVK thin film as hole transport and emissive layer. The diode consists of an indium tin oxide transparent conductive anode on a glass substrate, Os(II) complex doped PVK as hole transport and emissive layer, Bu-PBD as hole blocking/electron transport layer, a LiF layer as electron injecting layer and an aluminum cathode.

FIG. 6 shows an embodiment of the invention where an OLED is formed using Os(II) complexes of formula (4) doped PVK thin film as hole transport and emissive layer. The diode consists of an indium tin oxide transparent conductive anode on a glass substrate, Os(II) complex doped PVK as hole transport and emissive layer, a F-TBB layer as hole blocking layer, a $AlQ_3$ layer as electron transport layer, a LiF layer as electron injecting layer and an aluminum cathode.

FIG. 11 is an UV-vis absorption and normalized PL emission spectra of complexes Os1 (squares), Os2 (triangles), and Os3 (circles) in $CH_2Cl_2$ at room temperature.

DETAILED DESCRIPTION OF THE PREFERRED EMBODIMENTS

Figure 1:
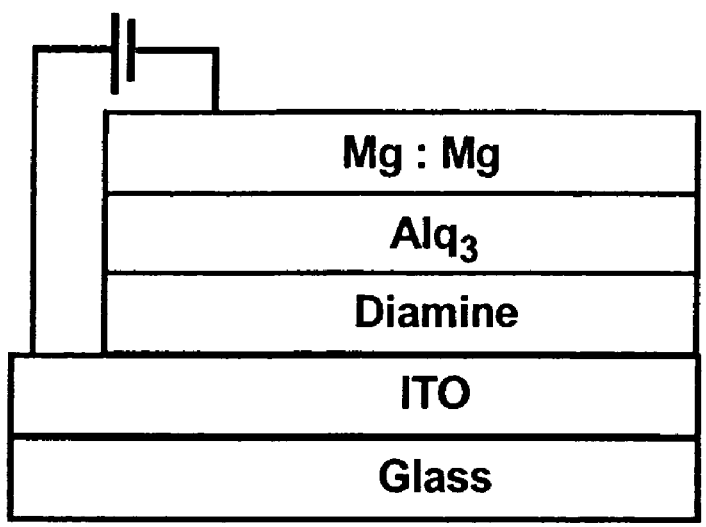
FIG. 1 is a depiction of a prior art small-molecule light-emitting diode.

The present invention is directed to Os(II) emissive molecules useful to display luminance when an electric voltage is applied to an OLED or PLED device in which they are employed, and to structures, and correlative molecules of the structures, that optimize the emission intensity and wavelength of the light emitting devices. On electroluminescence, this series of Os(II) molecules may produce emission which appears as either one of three primary colors of visible light; i.e. blue, green and red. It will be appreciated that, although the invention is described with reference to specific examples, it is not so limited, but is limited only by the attached claims. Moreover, although the description may make reference to possible mechanisms or modes of action, the invention is not limited to any given mechanism or mode of action.

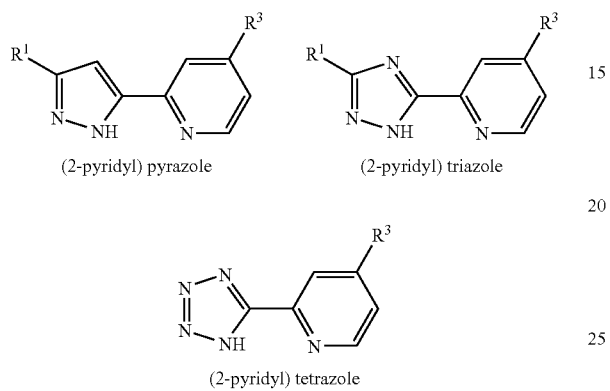

(2-pyridyl) pyrazole       (2-pyridyl) triazole (2-pyridyl) tetrazole

The ligands (2-pyridyl)pyrazole, (2-pyridyl) triazole and even (2-pyridyl) tetrazole can react with $Os_3(CO)_{12}$ to afford Os(II) metal complexes 1. The carbonyl ligands always adopt the cis geometry, and the trans-position to the CO ligands can be occupied by the anionic pyrazolate, triazolate or tetrazolate group. Moreover, the related Os(II) complexes of type 2 possess the CO ligands at the coordinative trans-position to the 2-pyridyl fragments can also be isolated as the co-products of lower yields.

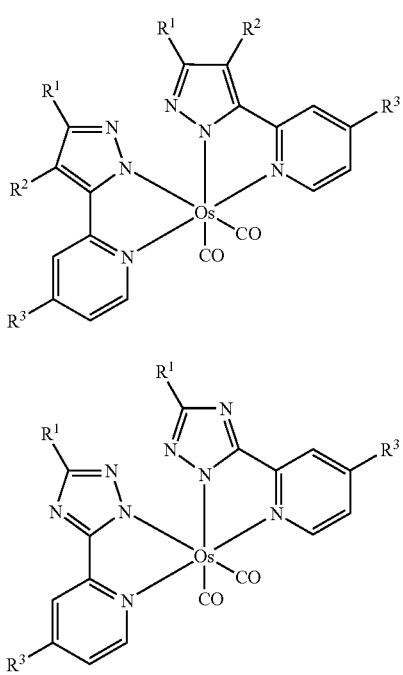

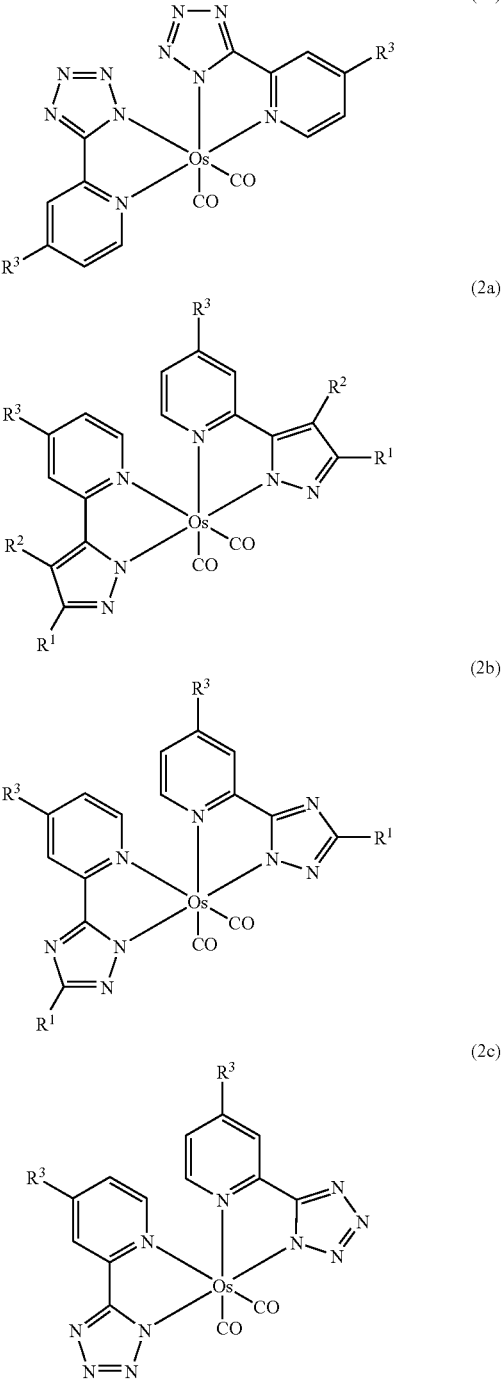

The hydrocarbon substituent $R^1$ can be methyl, methoxyl, dimethylamino, trifluoromethyl, t-butyl and phenyl group, while second $R^3$ can be methyl, methoxyl or any other organic functional groups so that tuning of the emission color can be successfully achieved. There is not restriction to the relative position of $R^3$ group on the 2-pyridyl fragment, as it can be located at all four possible positions of the 2-pyridyl fragment. Moreover, the hydrogen atom of the ligated pyrazolate fragments in 1a and 2a can be replaced by other small alkyl or aryl substituents, halide or pseudohalide group such as fluoride, chloride or even cyano functional group. The emission spectrum of these complexes shows the intra-ligand ππ* absorption band with distinct vibronic feature in the range 450~510 nm in both solid and fluid state. As a result, they could be served as the blue or cyanide blue phosphorescent emitters for various OLED applications. Fine adjustment of the emission color can be achieved by ligand functionalization. For example, substituting of $R^1$ group at the pyrazolate or triazolate fragment with certain strong electron withdrawing group would stabilize the HOMO of the chelating ligand. It would bring about the intra-ligand ππ* charge transfer transitions with higher energy, as can be seen from the hypsochromic shift in the $^3$ππ* phosphorescence spectra for this series of complexes. Concomitantly, substituting of $R^3$ group of 2-pyridyl group with strong electron donating property destabilizes the LUMO and also achieved the similar hypsochromic shift. The mechanistical aspects of color tuning as well as the photophysical properties of some related Os(II) metal complexes may be found in the article published by us; [Wu, P.-C. et al., *Organometallics* 2003, 22, 4938]. Absorption and emission properties of several Os(II) complexes with cis-arranged CO ligands are depicted in Table 1, while their individual molecular structures are given in Scheme 1.

The carbonyl ligands of complexes 1 and 2 can be replaced by a bidentate diamine or diimine ligand (N^N), such as ethylenediamine, tetramethylethylenediamine, 2,2'-bipyridine, 1,10-phenanthroline, 2-(2'-pyridyl)benzoxazole and their alkyl or aryl substituted derivatives, to afford complexes of type 3. These Os(II) complexes will retain the octahedral coordination arrangement with the nitrogen atoms occupying the original positions of the cis-CO ligands in both complexes 1 and 2. As the electron donor strength of the diimine ligands is far better than the π-acidic CO ligand, substantial red shift of phosphorescent emission compared with complexes 1 and 2 is expected.

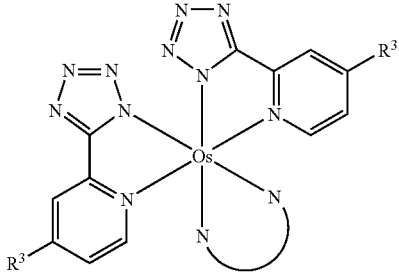

(3c)

Furthermore, upon treatment of complexes 1 and 2 with Me$_3$NO to remove the carbonyl ligands, followed by addition of donor ligand P such as phosphine, phosphite or arsine, the complexes of types 4 can be obtained in good yields. The cis-carbonyl arrangement has changed to the trans-donor ligand disposition during the substitution reaction. These complexes possess two (2-pyridyl)pyrazolate, triazolate or tetrazolate ligands located at the mutual planar position, and their emission is centered in the lower energy range of 610~660 nm, depending on the substituents $R^1$ and $R^3$ and the phosphine donor ligand P employed. This structural property has been unambiguously confirmed by the single crystal X-ray structural determination studies;

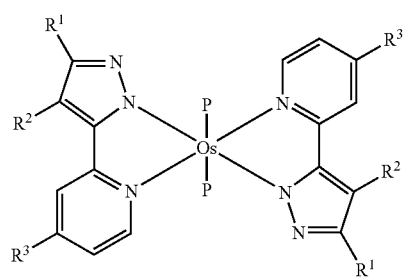

(4a)

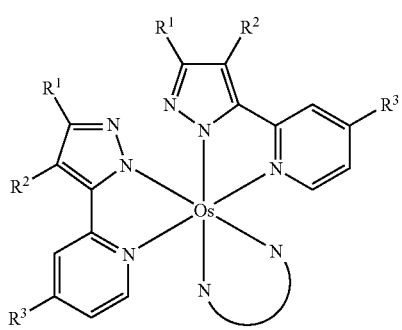

(3a)

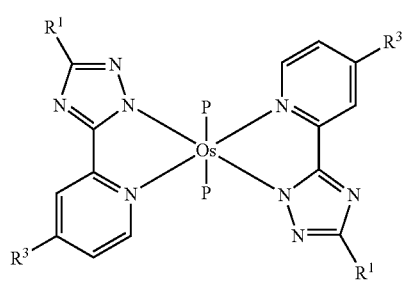

(4b)

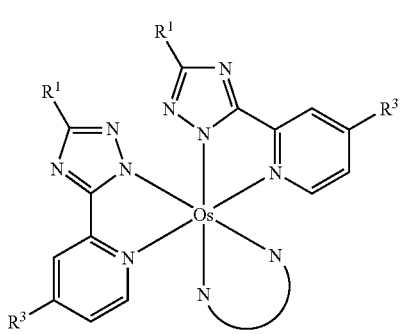

(3b)

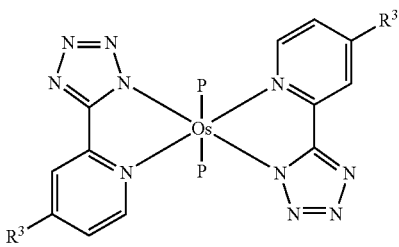

(4c)

The donor ligand P can be the phosphine ligand such as: PPh$_3$, PPh$_2$Me, PPhMe$_2$ and PMe$_3$, the phosphite ligand such as: P(OPh)$_3$ and P(OMe)$_3$, or even the arsine ligand such as AsPh$_3$ and AsMe$_3$. The PPh$_3$ derivatives tend to be less stable upon dissolution in organic solvents, compared with the Os(II) complexes possessing the slightly smaller and more electron donating phosphine ligands such as PPh$_2$Me and PPhMe$_2$. The emission wavelength is proportional to their relative donor strength; i.e. higher the donor strength, longer the emission wavelength. This is because that the observed phosphorescence originates primarily from the $^3$MLCT state, where the significant overlap of the 0-0 onsets between emission and the lowest energy absorption band, in combination with a relatively broad, structureless emission profile, provides the additional support to this spectral assignment. Absorption and emission properties of several Os(II) complexes with the trans-substituted phosphine ligands are depicted in Table 2. The summary of their molecular structures important for our current research is given in Scheme 2. It is notable that the compounds have shown short triplet lifetime in the microsecond range and different color emission between orange and deep red, and may also possess distinctive chemical properties. Thus, the modification to the basic structure in these molecules can systematically alter the emissive and chemical properties in desirable ways.

We may also use the above donor ligand containing at least one unsaturated functional group such as vinyl or allyl group, so that the resulting osmium complexes can be attached to a higher molecular weight polymer at the later stage. We may also use a polymer bound donor group so that we can incorporated our Os(II) fragment directly to the polymer. Moreover, derivations of these Os(II) complexes can be conducted using the established methods, for example, we can prepare the Os(II) complexes with a C—C double bond side chain, so that preparation of a doped copolymer will become feasible.

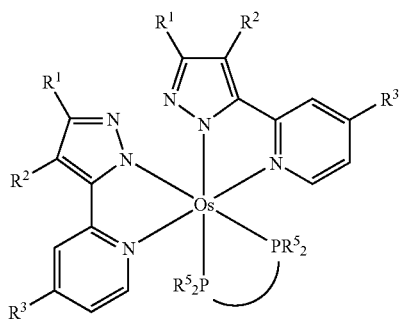

(5a)

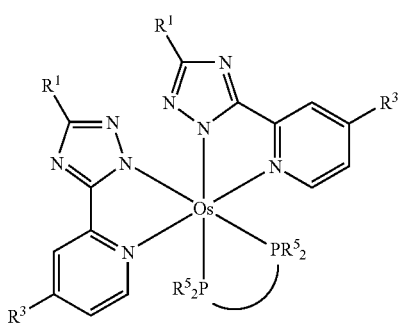

(5b)

-continued

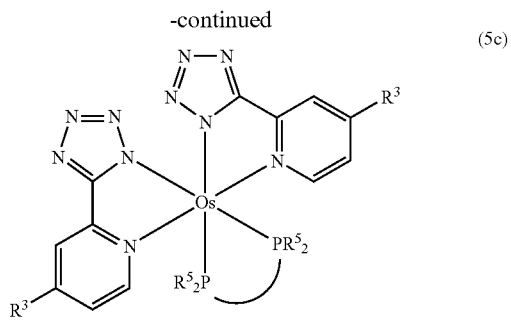

(5c)

The Os(II) metal complexes may also contain structures represented by any one of the formula 5. It is notable that the phosphorous atoms of the bidentate phosphine chelates preferably reside at the cis-disposition around the Os(II) metal center, which differs greatly from that depicted in the previous molecular formula 4, and the additional R$^5$ represents the alkyl and aryl substituents required for the diphosphine chelates employed. OLED and PLED devices fabricated using these Os(II) complexes would exhibit advantages such as good luminescence efficiency and good durability. The emission wavelength of complexes 5 would be more blue shifted compared with the diimine analogues 3, as the phosphorus atom appears to be a better π-acid compared with the nitrogen donor atom of diimine ligands. Moreover, other monoanionic chelating ligands may also be used in this invention to synthesize the Os(II) metal complexes showing the desired structural formula 1~5. Specific examples are illustrated below, using (2-pyridyl)pyrazolate ligand as reference to illustrate our basic design principle.

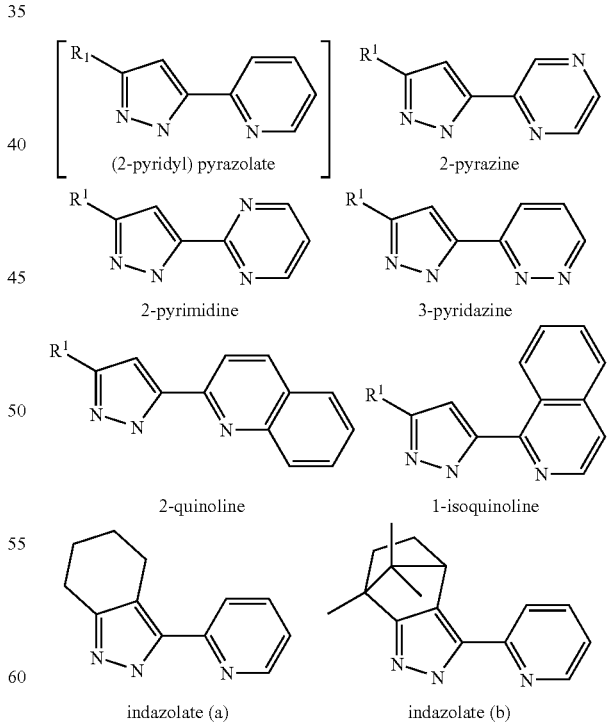

One may have other heterocyclic aromatic fragment to replace the 2-pyridyl fragment in building up all the required bidentate ligand. For example, the new heterocyclic fragment may consist of 2-pyrazine, 2-pyrimidine, 3-pyridazine, 2-quinoline and 1-isoquinoline molecule. Connecting these heterocyclic fragment to the above mentioned pyrazolate, triazolate or tetrazolate anionic fragment would produce an expended series of new chelating ligands that are equally suitable for synthesizing the required Os(II) emitters. Additional of an extra nitrogen atom to the backbone of 2-pyridyl fragment, e.g. giving formation of 2-pyrazine, 2-pyrimidine and 3-pyridazine group, is expected to cause a red-shifted emission compared with the Os(II) complexes possessing the parent (2-pyridyl)pyrazolate ligands. Incorporation of 2-quinoline and 1-isoquinoline fragment via increase the aromatic π-conjugation would also induce the similar bathochromatic shifting as expected from the basic photophysical theory. Moreover, the pyrazolate fragment can also be replaced by a bicyclic indazolate unit, for which greater solubility is expected due to the lipophilic cyclic hydrocarbon substituent. We expect that using this systematic tuning method would lead to the isolation of a wide range of highly emissive Os(II) based emitting materials.

The prior art device shown in FIG. 1 consists of a transparent Indium Tin Oxide (ITO) anode on a glass substrate, an aromatic diamine as the hole transport layer, an $AlQ_3$ (8-hydroxyquinoline aluminum) electron transport and emitter layer, and a Mg:Ag alloy cathode. When a sufficiently positive voltage is applied between the anode and the cathode, holes are injected from the anode, electrons are injected from the cathode and they recombine radiatively in the $AlQ_3$ emissive layer, producing light that is seen through the transparent anode and hole transport layer.

Figure 2:
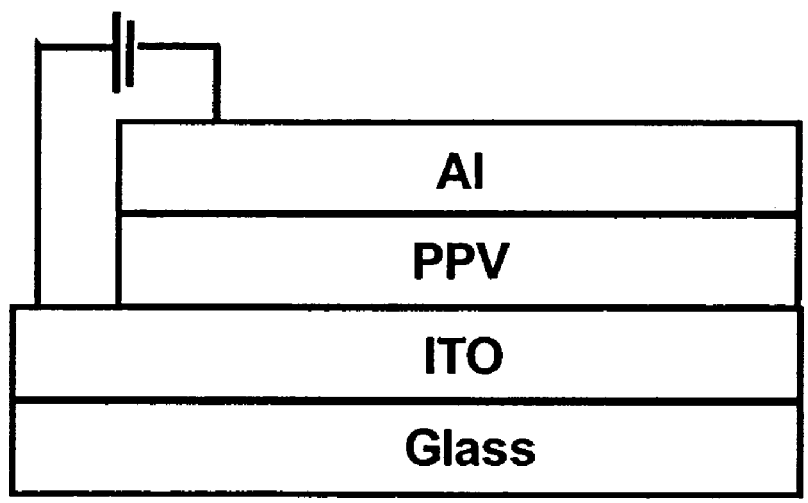
FIG. 2 is a depiction of a prior art polymer light-emitting diode.

The prior art device shown in FIG. 2 consists of a transparent ITO anode on a glass substrate, a thin PPV (poly(p-phenylenevinylene)) layer, and an Al cathode. When a sufficiently high positive voltage is applied between the anode and the cathode, holes are injected from the anode, electrons are injected from the cathode and they recombine radiatively in the PPV emissive layer, producing light that is seen through the transparent anode.

The prior art device shown in FIG. 3 consists of a transparent ITO anode on a glass substrate, a BTPD-PFCB hole transport layer, an ionic Os(II) compound doped PF-TPA-OXD emissive layer, and a Ca/Ag cathode. Under a positive bias voltage, efficient electroluminescent emission was observed. In this device count ions were present with the Os compound.

EXPERIMENTS

Without intending to limit it in any manner, the present invention will be further illustrated by the following examples.

Example 1

Synthesis of [Os(fppz)$_2$(CO)$_2$]

To a 50 mL reaction flask, it was charged with 3-trifluoromethyl-5-(2-pyridyl)pyrazole (fppzH, 296 mg, 1.39 mmol), pulverized Os$_3$(CO)$_{12}$ (200 mg, 0.22 mmol), and 25 mL of anhydrous diethylene glycol monoethyl ether. The solution was maintained at 180~190° C. for 24 hours. After then, the solvent was evaporated and the solid material was sublimed under reduced pressure (300 mtorr/210° C.). The sublimate was further crystallized from a mixture of CH$_2$Cl$_2$ and hexane, giving the product [Os(fppz)$_2$(CO)$_2$] as colorless needle-like crystals (267 mg, 0.40 mmol) in 60% yield.

Spectral data: MS (EI, $^{192}$Os): m/z 672 (M$^+$), 616 (M$^+$−2CO). IR(CH$_2$Cl$_2$): v(CO), 2043 (s), 1973 (s) cm$^{-1}$. $^1$H NMR (500 MHz, d$_6$-acetone, 294K): δ 9.17 (ddd, J$_{HH}$=6.0, 1.5, 1.0 Hz), 8.20 (ddd, J$_{HH}$=8.0, 8.0, 1.5 Hz), 8.10 (ddd, J$_{HH}$=8.0, 1.5, 1.0 Hz), 7.48 (ddd, J$_{HH}$=8.0, 6.0, 1.5 Hz), 7.10 (s). $^{13}$C NMR (125 MHz, d$_6$-acetone): δ 177.6 (CO), 157.1 (CH), 155.8 (C), 151.7 (C), 144.1 (q, $^2$J$_{CF}$=35.5 Hz, C), 141.3 (CH), 125.2 (CH), 123.1 (q, $^1$J$_{CF}$=265.7 Hz, CF$_3$), 121.6 (CH), 103.4 (CH). $^{19}$F NMR (470 MHz, d$_6$-acetone): δ −60.2 (s). Anal. Calcd. for C$_{20}$H$_{10}$F$_6$N$_6$O$_2$OS: C, 35.82; N, 12.53; H, 1.50. Found: C, 35.67; N, 12.84; H, 1.78.

Example 2

Synthesis of [Os(fmpz)$_2$(CO)$_2$]

3-Trifluoromethyl-5-(4-methyl-2-pyridyl)pyrazole (fmpzH, 240 mg, 1.04 mmol) and finely pulverized Os$_3$(CO)$_{12}$ (150 mg, 0.165 mmol) were loaded in a 25 mL Carius tube and degassed. It was then sealed under vacuum and placed in an oven maintained at temperatures 180~185° C. for 2.5 days, during which time its color changed gradually from light yellow to red-brown and finally to orange yellow. After stopped the reaction, the tube was cooled, opened and the content was dissolved in acetone. The insoluble material was filtered off, and the filtrate was dried under vacuum and the residue was sublimed (0.24 torr, 220° C.). The product was then subjected to recrystallization in CH$_2$Cl$_2$ and hexane, giving [Os(fmpz)$_2$(CO)$_2$] as colorless needle-like crystals (34 mg, 0.048 mmol) in 29% yield.

Spectral data: MS (EI, $^{192}$Os): m/z 700 (M$^+$), 644 (M$^+$−2CO). IR(CH$_2$Cl$_2$): v(CO), 2041 (s), 1970 (s) cm$^{-1}$. $^1$H NMR (400 MHz, d$_6$-acetone, 294K): 8.97 (d, J$_{HH}$=6.0 Hz), 7.95 (s), 7.31 (d, J$_{HH}$=6.0 Hz), 7.06 (s), 2.58 (s, Me). $^{13}$C NMR (125 MHz, d$_6$-acetone, 294K): 177.8 (2CO), 156.2 (2C), 155.2 (2C), 153.7 (2C), 151.8 (2C), 144.0 (q, $^2$J$_{CF}$=35.4 Hz, 2C), 126.2 (2CH), 122.3 (q, $^1$J$_{CF}$=241.8 Hz, 2CF$_3$), 122.1 (2CH), 103.1 (2CH), 21.2 (2Me). $^{19}$F NMR (470 MHz, d$_6$-acetone, 294K): 59.8 (s). Anal. Calcd. For C$_{22}$H$_{14}$F$_6$N$_6$O$_2$Os: C, 37.82; N, 12.03; H, 2.02. Found: C, 37.69; N, 12.01; H, 2.08.

Example 3

Synthesis of [Os(bptz)$_2$(CO)$_2$]

To a 50 mL reaction flask, it was charged with 3-t-butyl-5-(2-pyridyl) 1,2,4-triazole (bptzH, 273 mg, 1.35 mmol), pulverized Os$_3$(CO)$_{12}$ (200 mg, 0.22 mmol), and 25 mL of anhydrous diethylene glycol monoethyl ether. The solution was maintained at 180° C. for 24 hours. After then, the solvent was evaporated and the residue was washed with water. The crude product was crystallized from a mixture of acetone and hexane, giving [Os(bptz)$_2$(CO)$_2$] as colorless block-shaped crystals (309 mg, 0.48 mmol) in 72% yield.

Spectral data: MS (EI, $^{192}$Os): m/z 651 (M$^+$), 591 (M$^+$−2CO). IR(CH$_2$Cl$_2$): v(CO), 2041 (s), 1970 (s) cm$^{-1}$. $^1$H NMR (400 MHz, acetone-d$_6$, 298K): δ 9.16 (dd, J$_{HH}$=6.8, 1.2 Hz), 8.25 (ddd, J$_{HH}$=7.4, 6.8, 1.2 Hz), 8.10 (dd, J$_{HH}$=7.4, 1.2 Hz), 7.55 (ddd, J$_{HH}$=6.8, 7.4, 1.2 Hz), 1.12 (s, $^t$Bu). Anal. Calcd for C$_{24}$H$_{26}$N$_8$O$_2$OS: C, 44.43; N, 17.27; H, 4.04. Found: C, 44.26; N, 17.60; H, 4.30.

Example 4

Synthesis of [Os(fptz)$_2$(CO)$_2$]

To a 50 mL reaction flask, it was charged with 3-trifluoromethyl-5-(2-pyridyl) 1,2,4-triazole (fptzH, 298 mg, 1.39 mmol), pulverized Os$_3$(CO)$_{12}$ (200 mg, 0.22 mmol), together with 20 mL of anhydrous diethylene glycol monoethyl ether. The solution was maintained at 180~190° C. for 24 hours. After then, the solvent was evaporated under vacuum, and the residue sublimed under reduced pressure (300 mtorr/220° C.). The sublimate was crystallized from a mixture of $CH_2Cl_2$ and hexane, giving $[Os(fptz)_2(CO)_2]$ as colorless needle-like crystals (268 mg, 0.40 mmol) in 60% yield.

Spectral data: MS (EI, $^{192}Os$): m/z 674 ($M^+$), 618 ($M^+$–2CO). IR($CH_2Cl_2$): v (CO), 2054 (s), 1986 (s) $cm^{-1}$. $^1H$ NMR (400 MHz, $CDCl_3$, 298K): δ 9.01 (dd, $J_{HH}$=6.7, 0.8 Hz), 8.32 (dd, $J_{HH}$=7.6, 0.8 Hz), 8.17 (ddd, $J_{HH}$=7.6, 6.7, 0.8 Hz), 7.51 (ddd, $J_{HH}$=6.7, 7.6, 0.8 Hz). Anal. Calcd for $C_{18}H_8F_6N_8O_2Os$: C, 32.15; N, 16.66; H, 1.20. Found: C, 32.02; N, 16.87; H, 1.53.

Example 5

Synthesis of $[Os(fppz)_2(PPh_2Me)_2]$, (Os1)

To a 50 mL reaction flask, it was charged with 3-trifluoromethyl-5-(2-pyridyl)pyrazole (fppzH, 292 mg, 1.37 mmol), pulverized $Os_3(CO)_{12}$ (200 mg, 0.22 mmol), and 20 mL of anhydrous diethylene glycol monoethyl ether (DGME). The mixture was heated at 180~190° C. for 24 hours. After then, the temperature was lowered to ~150° C., freshly sublimed $Me_3NO$ (120 mg, 1.59 mmol) dissolved in 12 mL of DGME was added, and stirring was continued for 5 min. Finally, $PPh_2Me$ (592 μL, 3.18 mmol) was injected into the mixture. In the meantime, the temperature of solution was raised up to 190° C. After 12 hours, the reaction was stopped, the solvent evaporated under vacuum, and the residue washed with distilled water (20 mL×2) to remove the remaining $Me_3NO$. Further purification was conducted using silica gel column chromatography (EA:hexane=1:1), followed by recrystallization from a mixture of EA and hexane at room temperature, giving bright red crystalline solid (436 mg, 0.43 mmol) in 65% yield.

Spectral data: MS (EI, $^{192}Os$): m/z 1014 ($M^+$), 814 ($M^+$–$PPh_2Me$), 616 ($M^+$–$2PPh_2Me$). $^1H$ NMR (400 MHz, $d_6$-acetone): δ 10.40 (d, 2H, $J_{HH}$=6.0 Hz), 7.32 (ddd, 2H, $J_{HH}$=7.6, 6.0, 1.2 Hz), 7.15~6.84 (m, 20H), 6.73 (s, 2H), 6.66~6.14 (m, 4H), 1.16 (t, 6H, $J_{HP}$=3.2 Hz, $CH_3$). $^{19}F$ NMR (470 MHz, $d_6$-acetone): δ −59.8 (s). $^{31}P$ NMR (202 MHz, $d_6$-acetone): δ −17.4 (s). Anal. Calcd. for $C_{44}H_{36}F_6N_6P_2Os$: C, 52.07; N, 8.28; H, 3.58. Found: C, 51.99; N, 8.17; H, 3.78.

Example 6

Synthesis of $[Os(fppz)(PPhMe_2)]$, (Os2)

The procedures of EXAMPLE 5 were followed, starting from 3-trifluoromethyl-5-(2-pyridyl)pyrazole (fppzH, 292 mg, 1.37 mmol), powdery $Os_3(CO)_{12}$ (200 mg, 0.22 mmol), freshly sublimed $Me_3NO$ (125 mg, 1.60 mmol) and phosphine ligand $PPhMe_2$ (460 μL, 3.19 mmol), the title compound $[Os(fppz)_2(PPhMe_2)_2]$ was obtained as bright red crystalline solid (371 mg, 0.42 mmol); yield: 63%.

Spectral data: MS (FAB, $^{192}Os$): m/z 892 ($M^+$), 754 ($M^+$–$PPhMe_2$), 616 ($M^+$–$2PPhMe_2$). $^1H$ NMR (400 MHz, $d_6$-acetone): δ 10.31 (d, 2H, $J_{HH}$=6.6 Hz), 7.56~7.48 (m, 4H), 7.07~7.03 (m, 2H), 6.94~6.87 (m, 8H), 6.42~6.38 (m, 4H), 0.80 (t, 6H, $J_{HP}$=3.6 Hz, $CH_3$), 0.59 (t, 6H, $J_{HP}$=3.2 Hz, $CH_3$). $^{19}F$ NMR (470 MHz, $d_6$-acetone): δ −59.5 (s). $^{31}P$ NMR (202 MHz, $d_6$-acetone): δ −19.6 (s). Anal. Calcd. for $C_{34}H_{32}F_6N_6OsP_2$: C, 45.84; N, 9.43; H, 3.62. Found: C, 46.00; N, 9.32; H, 3.81.

Example 7

Synthesis of $[Os(fppz)_2(P''Bu_3)_2]$

The procedures of EXAMPLE 5 were followed, starting from 3-trifluoromethyl-5-(2-pyridyl)pyrazole (fppzH, 148 mg, 0.69 mmol), powdery $Os_3(CO)_{12}$ (100 mg, 0.11 mmol), freshly sublimed $Me_3NO$ (60 mg, 0.80 mmol) and phosphine ligand $P''Bu_3$ (330 μL, 1.32 mmol), the title compound $[Os(fppz)_2(P''Bu_3)_2]$ was obtained as air sensitive, dark red solid (61 mg, 0.06 mmol); yield: 19%.

Spectral Data: $^1H$ NMR (400 MHz, $d_6$-acetone): δ 10.74 (br, 2H), 7.89 (d, 2H, $J_{HH}$=8.0 Hz), 7.79 (dd, 2H, $J_{HH}$=8.0, 7.4 Hz), 7.17 (dd, 2H, $J_{HH}$=7.4, 6.4 Hz), 7.11 (s, 2H), 0.97~0.65 (m, 54H, ″Bu). $^{19}F$ NMR (470 MHz, $d_6$-acetone): δ −59.2 (s). $^{31}P$ NMR (202 MHz, $d_6$-acetone): δ −24.7 (s).

Example 8

Synthesis of $[Os(bppz)_2(PPh_2Me)_2]$

The procedures of EXAMPLE 5 were followed, starting from 3-t-butyl-5-(2-pyridyl)pyrazole (bppzH, 280 mg, 1.39 mmol), powdery $Os_3(CO)_{12}$ (200 mg, 0.22 mmol), freshly sublimed $Me_3NO$ (118 mg, 1.58 mmol) and phosphine $PPh_2Me$ (595 μL, 3.19 mmol), the title compound $[Os(bppz)_2(PPh_2Me)_2]$ was obtained as dark red crystalline solid (393 mg, 0.40 mmol); yield: 60%.

Spectral data: MS (FAB, $^{192}Os$): m/z 992 ($M^+$), 792 ($M^+$–$PPh_2Me$), 607 ($M^+$–$2PPh_2Me$). $^1H$ NMR (400 MHz, $CDCl_3$): δ 10.41 (br, 2H), 7.22 (d, 4H, $J_{HH}$=7.2 Hz), 7.08 (dd, 4H, $J_{HH}$=7.4, 7.6 Hz), 7.00~6.97 (m, 6H), 6.87 (d, 2H, $J_{HH}$=7.6 Hz), 6.80 (dd, 2H, $J_{HH}$=7.6, 7.4 Hz), 6.57~6.50 (m, 6H), 6.13 (br, 2H), 1.60 (s, 18H), 1.02 (br, 6H). Anal. Calcd. For $C_{50}H_{54}N_6OsP_2$: C, 60.59; N, 8.48; H, 5.49. Found: C, 60.41; N, 8.57; H, 5.60.

Example 9

Synthesis of $[Os(pppz)_2(PPh_2Me)_2]$

The procedures of EXAMPLE 5 were followed, starting from 3-phenyl-5-(2-pyridyl)pyrazole (pppzH, 307 mg, 1.39 mmol), powdery $Os_3(CO)_{12}$ (200 mg, 0.22 mmol), freshly sublimed $Me_3NO$ (125 mg, 1.61 mmol) and the phosphine $PPh_2Me$ (600 μL, 3.20 mmol), the title compound $[Os(pppz)_2(PPh_2Me)_2]$ was obtained as dark red crystalline solid (375 mg, 0.36 mmol) in 54% yield.

Analytical data: MS (FAB, $^{192}Os$): m/z 1032 ($M^+$), 831 ($M^+$–$PPh_2Me$), 631 ($M^+$–$2PPh_2Me$). Anal. Calcd. for $C_{54}H_{46}N_6OsP_2$: C, 62.90; N, 8.15; H, 4.50. Found: C, 62.65; N, 8.02; H, 4.61.

Example 10

Synthesis of $[Os(fptz)_2(PPh_3)_2]$

The procedures of EXAMPLE 5 were followed, starting from 3-trifluoromethyl-5-(2-pyridyl) 1,2,4-triazole (fptzH, 298 mg, 1.39 mmol), powdery $Os_3(CO)_{12}$ (200 mg, 0.22 mmol), freshly sublimed $Me_3NO$ (160 mg, 2.12 mmol) and the phosphine $PPh_3$ (1.10 g, 4.23 mmol), the title compound $[Os(fptz)_2(PPh_3)_2]$ was obtained as bright orange power (355 mg, 0.31 mmol) in 47% yield.

Analytical data: MS (FAB, $^{192}Os$): m/z 1143 ($M^+$), 618 ($M^+$–$2PPh_3$). Anal. Calcd. for $C_{52}H_{38}F_6N_8OsP_2$: C, 54.73; N, 9.82; H, 3.36. Found: C, 54.85; N, 9.76; H, 3.50.

Example 11

Synthesis of [Os(fptz)$_2$(PPh$_2$Me)$_2$], (Os3)

The procedures of EXAMPLE 5 were followed, starting from 3-trifluoromethyl-5-(2-pyridyl) 1,2,4-triazole (fptzH, 298 mg, 1.39 mmol), powdery Os$_3$(CO)$_{12}$ (200 mg, 0.22 mmol), freshly sublimed Me$_3$NO (121 mg, 1.59 mmol) and phosphine PPh$_2$Me (595 µL, 3.19 mmol), the title compound [Os(fptz)$_2$(PPh$_2$Me)$_2$] was obtained as bright red crystalline solid (504 mg, 0.50 mmol) in 75% yield.

Spectral data: MS (FAB, $^{192}$Os): m/z 1018 (M$^+$), 818 (M$^+$−PPh$_2$Me), 618 (M$^+$−2PPh$_2$Me). $^1$H NMR (400 MHz, d$_6$-acetone): δ 10.26 (d, 2H, JHH=6.8 Hz), 7.54 (ddd, 2H, JHH=6.8, 7.6, 0.8 Hz), 7.29 (d, 2H, JHH=7.6, 0.8 Hz), 7.21 (ddd, 2H, JHH=7.6, 6.8, 0.8 Hz), 7.24~7.10 (m, 4H), 7.00 (t, 4H, JHH=7.6 Hz), 6.92 (t, 4H, JHH=7.6 Hz), 6.89~6.84 (m, 4H), 6.69~6.60 (m, 4H), 1.24 (t, 6H, J$_{HP}$=3.4 Hz, CH$_3$). Anal. Calcd. for C$_{42}$H$_{34}$F$_6$N$_8$OsP$_2$: C, 49.60; N, 11.02; H, 3.37. Found: C, 49.61; N, 10.98; H, 3.50.

Example 12

Synthesis of [Os(bptz)$_2$(PPh$_2$Me)$_2$]

The procedures of EXAMPLE 5 were followed, starting from 3-t-butyl-5-(2-pyridyl) 1,2,4-triazole (bptzH, 281 mg, 1.39 mmol), powdery Os$_3$(CO)$_{12}$ (200 mg, 0.22 mmol), freshly sublimed Me$_3$NO (117 mg, 1.57 mmol) and the phosphine PPh$_2$Me (596 µL, 3.19 mmol), the title compound [Os(bptz)$_2$(PPh$_2$Me)$_2$] was obtained as dark red crystalline solid (401 mg, 0.40 mmol) in 61% yield.

Spectral data: MS (FAB, $^{192}$Os): m/z 994 (M$^+$), 794 (M$^+$−PPh$_2$Me), 594 (M$^+$−2PPh$_2$Me). $^1$H NMR (500 MHz, d$_4$-methanol): δ 10.37 (d, 2H, J$_{HH}$=4.8 Hz), 7.34 (d, 4H, J$_{HH}$=4.8 Hz), 7.09~6.86 (m, 18H), 6.62~6.59 (m, 4H), 1.63 (s, 18H, $^t$Bu), 0.90 (s, 6H, Me). $^{31}$P NMR (202 MHz, d$_4$-methanol): δ 19.6 (s). Anal. Calcd. for C$_{48}$H$_{52}$N$_8$P$_2$Os: C, 58.05; N, 11.28; H, 5.28. Found: C, 57.71; N, 11.43; H, 5.40.

Example 13

Synthesis of [Os(hptz)$_2$(PPh$_2$Me)$_2$]

The procedures of EXAMPLE 5 were followed, starting from 3-heptafluoropropyl-5-(2-pyridyl) 1,2,4-triazole (hp-pzH, 430 mg, 1.37 mmol), powdery Os$_3$(CO)$_{12}$ (200 mg, 0.22 mmol), freshly sublimed Me$_3$NO (120 mg, 1.59 mmol) and the phosphine PPh$_2$Me (592 µL, 3.18 mmol), the title compound [Os(hptz)$_2$(PPh$_2$Me)$_2$] was obtained as bright orange crystalline solid (586 mg, 0.48 mmol) in 73% yield.

Spectral data: MS (FAB, $^{192}$Os): m/z 1219 (M$^+$), 1019 (M$^+$−PPh$_2$Me), 818 (M$^+$−2PPh$_2$Me). $^1$H NMR (400 MHz, d$_6$-acetone): δ 10.24 (d, 2H, J$_{HH}$=6.8 Hz), 7.49 (dd, 2H, J$_{HH}$=6.8, 7.6 Hz), 7.30 (d, 2H, J$_{HH}$=7.6 Hz), 7.18~7.14 (m, 4H), 7.10~7.03 (m, 10H), 6.88 (t, 4H, J$_{HH}$=7.4 Hz), 6.59~6.55 (m, 4H), 1.22 (t, 6H, J$_{HP}$=3.2 Hz, CH$_3$). $^{19}$F NMR (470 MHz, d$_6$-acetone): δ −122.6 (s, 4F), −109.7 (q, 4F, J$_{FF}$=10.0 Hz), −79.8 (t, 6F, J$_{FF}$=10.0 Hz). $^{31}$P NMR (202 MHz, d$_6$-acetone): 6-18.2 (s). Anal. Calcd for C$_{46}$H$_{34}$F$_{14}$N$_8$OsP$_2$: C, 45.40; N, 9.21; H, 2.82. Found: C, 45.41; N, 9.27; H, 2.98.

Example 14

Synthesis of [Os(hptz)$_2$(PPhMe$_2$)$_2$]

The procedures of EXAMPLE 5 were followed, starting from 3-heptafluoropropyl-5-(2-pyridyl) 1,2,4-triazole (hp-pzH, 430 mg, 1.37 mmol), powdery Os$_3$(CO)$_{12}$ (200 mg, 0.22 mmol), freshly sublimed Me$_3$NO (122 mg, 1.60 mmol) and the phosphine PPhMe$_2$ (460 µL, 3.20 mmol), the title compound [Os(hptz)$_2$(PPhMe$_2$)$_2$] was obtained as bright orange crystalline solid (506 mg, 0.46 mmol) in 70% yield.

Spectral data: MS (FAB, $^{192}$Os): m/z 1095 (M$^+$), 957 (M$^+$ (PPhMe2), 8618 (M+(2PPhMe2). 1H NMR (400 MHz, d6-acetone): (10.12 (d, 2H, JHH=6.4 Hz), 7.73 (dd, 2H, J$_{HH}$=6.4, 7.4 Hz), 7.68~7.65 (m, 2H), 7.20 (ddd, 2H, J$_{HH}$=7.4, 6.4, 1.6 Hz), 7.08 (t, 2H, J$_{HH}$=7.6 Hz), 6.90 (t, 4H, J$_{HH}$=7.6 Hz), 6.38~6.33 (m, 4H), 0.86 (t, 6H, J$_{HP}$=3.2 Hz, CH$_3$), 0.61 (t, 6H, J$_{HP}$=3.2 Hz, CH$_3$). $^{19}$F NMR (470 MHz, d$_6$-acetone): δ −126.1 (s, 4F), −110.1 (q, 4F, J$_{FF}$=8.3 Hz), −80.0 (t, 6F, J$_{FF}$=8.3 Hz). $^{31}$P NMR (202 MHz, d$_6$-acetone): δ −22.1 (s). Anal. Calcd for C$_{36}$H$_{30}$F$_{14}$N$_8$OsP$_2$: C, 39.57; N, 10.25; H, 2.77. Found: C, 39.43; N, 10.20; H, 2.90.

Example 15

Synthesis of [Os(fppz)$_2$(dppe)]

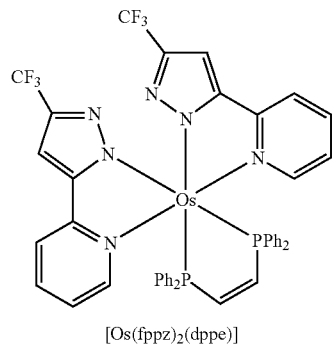

[Os(fppz)$_2$(dppe)]

To a 50 mL reaction flask, it was charged with 3-trifluoromethyl-5-(2-pyridyl)pyrazole (fppzH, 292 mg, 1.37 mmol), pulverized Os$_3$(CO)$_{12}$ (200 mg, 0.22 mmol), and 20 mL of anhydrous diethylene glycol monoethyl ether (DGME). The mixture was heated at 180~190° C. for 24 hours. After then, the temperature was lowered to ~150° C., freshly sublimed Me$_3$NO (150 mg, 2.00 mmol) dissolved in 12 mL of DGME was added, and stirring was continued for 5 min. Finally, cis-1,2-bis(diphenylphosphino)ethylene (dppe, 626 mg, 1.58 mmol) was added into the mixture. In the meantime, the temperature of solution was raised up to 210° C. After 24 hours, the reaction was stopped, the solvent evaporated under vacuum, and the residue washed with distilled water (20 mL×2) to remove the remaining Me$_3$NO. Further purification was conducted using silica gel column chromatography (EA:hexane=1:1), followed by recrystallization from a mixture of EA and hexane at room temperature, giving yellow crystalline solid (310 mg, 0.31 mmol) in 47% yield.

Spectral data: MS (FAB, $^{192}$Os): m/z 1012 (M$^+$). $^1$H NMR (500 MHz, d$_6$-acetone): δ 7.91~7.88 (m, 6H), 7.61 (dd, 2H, J$_{HH}$=7.5, 7.8 Hz), 7.54 (d, 2H, J$_{HH}$=7.5 Hz), 7.34 (dd, 2H, J$_{HH}$=7.8, 7.3 Hz), 7.26~7.23 (m, 4H), 7.05 (d, 2H, J$_{HH}$=7.3

Hz), 7.01 (d, 2H, $J_{Hp}$=6.0 Hz), 6.82 (q, 6H, $J_{HH}$=7.4 Hz), 6.71 (s, 2H), 6.69 (t, 4H, $J_{Hh}$=7.4 Hz). Anal. Calcd for $C_{44}H_{32}F_6N_6OsP_2$: C, 52.28; N, 8.31; H, 3.19. Found: C, 52.31; N, 8.27; H, 3.27.

Example 16

Demonstration of efficient phosphorescent polymer light Emitting Diodes

In this embodiment of the invention, shown in FIG. 4, three double-layer organic light emitting diodes were fabricated using commercial ITO-coated (120 nm) glass substrates with a sheet resistance of 15 ohm/□ (Applied Films Corp.). The device structure consisted of an Os complex doped PVK layer as the hole-transport and emissive layer (Os(II) complexes Os1: $Os(fppz)_2(PPh_2Me)_2$, Os2: $Os(fppz)_2(PPhMe_2)_2$, and Os3: $Os(bptz)_2(PPh_2Me)_2$ were chosen to be used in three separate devices), spin-coated from its chloroform solution (0.6 mg: 6 mg/ml) at 1500 rpm for 60". The thickness of the resulting films was measured on a Dektak surface profilometer, and found to be around 60 nm. A vacuum deposited 2-(4-biphenylyl-5-(4-tert-butylphenyl)-1,3,4-oxadiazole (PBD) layer (20 nm) was used as a hole-blocking/electron transport layer. The device fabrication was completed by the evaporation of LiF (1 nm) and aluminum cathode (150 nm). The electroluminescence spectra, luminance-voltage, efficiency-voltage characteristics of the three devices are shown in FIG. 5 and Table 3. The diodes emit red light with emission peaks in the range of 626 to 658 nm. No excimer or exciplex emission was observed.

Example 17

Further demonstration of efficient phosphorescent polymer Light Emitting Diodes

In another embodiment of the invention shown in FIG. 6, a THREE-layer organic light emitting diode was fabricated using commercial ITO-coated (120 nm) glass substrates with a sheet resistance of 15 ohm/□ (Applied Films Corp.). The device structure consisted of an Os complex doped PVK layer as the hole-transport and emissive layer (three compounds shown in formula (I) were used in three separate device), spin-coated from its chloroform solution (0.6 mg: 6 mg/ml) at 1500 rpm for 60". The thickness of the resulting films was measured on a Dektak surface profilometer, and found to be around 60 nm. A vacuum deposited 1,3,5-tris(4'-fluoro-biphenyl-4-yl)benzene (F-TBB) layer (15 nm) was used as a hole-blocking layer and a vacuum deposited AlQ3 layer was used as an electron transport layer. The device fabrication was completed by the evaporation of LiF (1 nm) and aluminum cathode (150 nm).

Figure 7A:
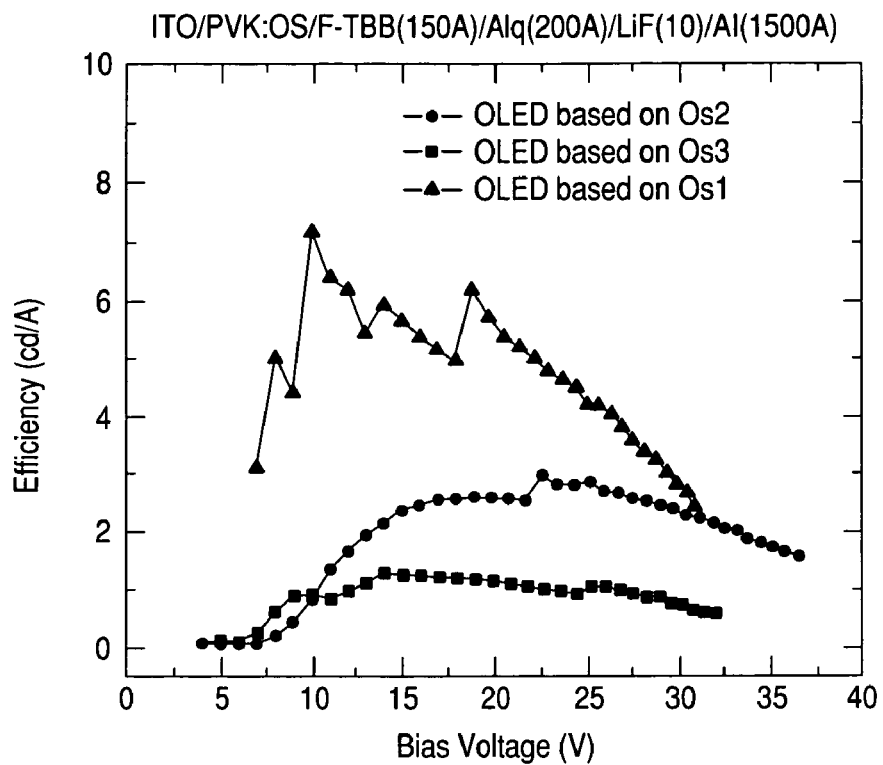
FIG. 7 is a pair of graphical depictions of the luminescence-voltage, efficiency-voltage characteristics of the embodiment of FIG. 6.
Figure 7B:
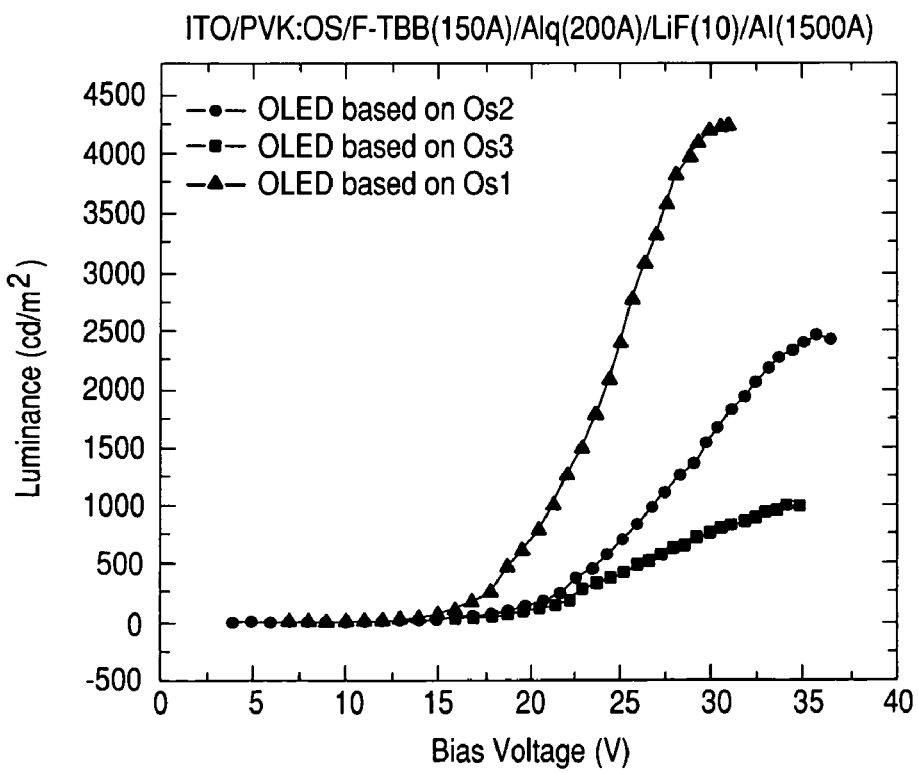

The luminance-voltage, efficiency-voltage characteristics of the three devices are shown in FIG. 7 and Table 4. The electroluminescence spectra of the diodes were identical to those of shown in FIG. 5. No excimer or exciplex emission was observed. Since PBD is a relatively low crystallization temperature, it is not an ideal candidate for use as hole blocking/electron transport layer, in this example it was replaced by a new hole blocking layer F-TBB (Ref. on F-TBB: K. Okumoto et al. Chem. Mater. 15, 699 (2003)). The device performance has been improved, especially for Os1 based devices. Maximum luminous efficiencies reached 7.0 cd/A, 3.5 cd/A, and 1.2 cd/A for devices based on 10 wt. % of Os(II) complexes Os1, Os2 and Os3, respectively, even with air stable aluminum as the cathode. Some photophysical and electrochemical properties of these three Os(II) complexes are listed in Table 5.

Example 18

Further demonstration of efficient polymer phosphorescent Light Emitting Diodes at Different Doping Concentrations The dependence of electroluminescent performance on the doping levels of Os(II) complexes in the emitting layer was investigated in this embodiment using the same device structure as in Example 16, but at different doping concentrations. Similar to most reported electrophosphorescent OLEDs and PLEDs, the device performance showed a strong dependence on doping concentration. The results are summarized in Table 6. The best device performance was observed at 10 wt. % doping concentration for all three Os(II) complexes. The maximum luminance and luminous efficiency increased with increasing Os(II) complex concentration in the beginning and reached maxima at 10 wt. % doping concentration. However, a further increase in the doping level resulted in a reduction in both device brightness and efficiency probably due to concentration quenching and triplet-triplet annihilation.

Figure 8:
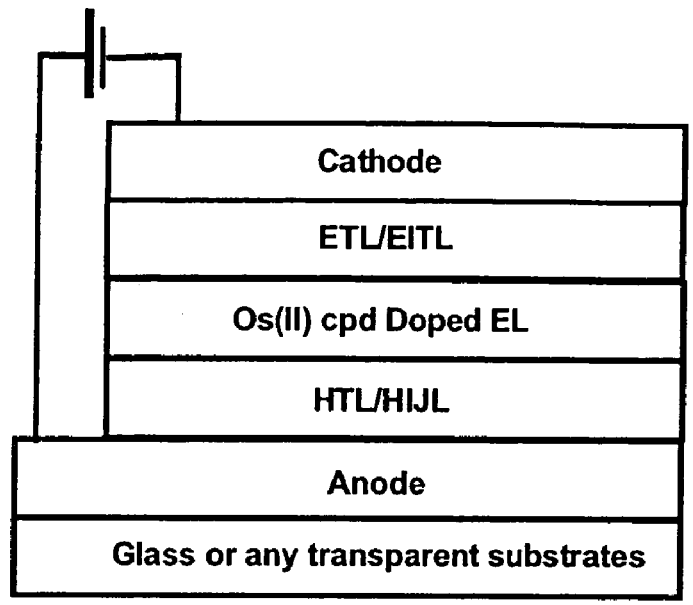
FIG. 8 is a depiction of a generic normal fashion OLED/PLED device configuration.
Figure 9:
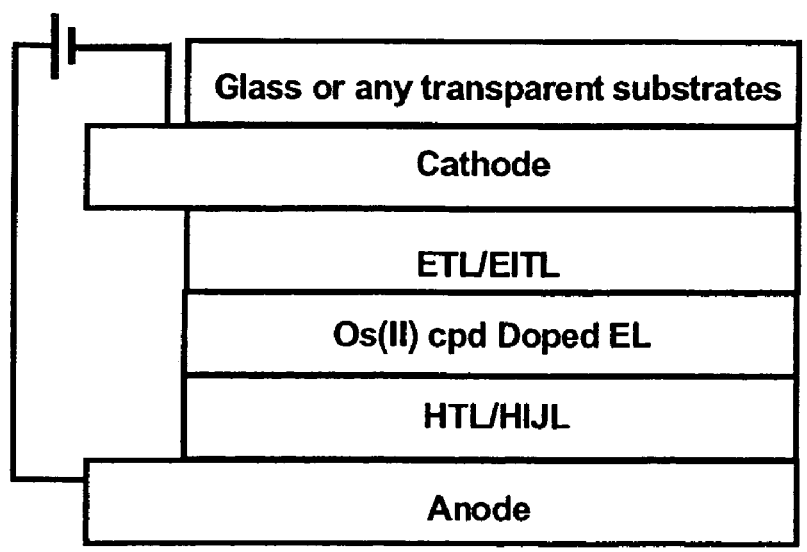
FIG. 9 is a depiction of a generic "reverse" structured OLED/PLED device configuration.

The application of the Os(II) complexes to light emitting diodes is not limited by the previously mentioned devices configuration. Since this is a new class of efficient phosphorescent materials, they can be used in variety of device structures. Some examples are given in FIGS. 8 and 9, where the cathode can be any high conductivity and low work function materials, electron transport layer (ETL) and electron injecting layer (EIJL) can be a single ETL; hole transport layer (HTL) and hole injecting layer (HIJL) can be a single HTL. The anode can be any high conductivity and high work function materials. Depending on the transport properties of the host material, Os compound doped emissive layer (EL) can also function as a EL/HTL layer or a EL/ETL layer. According to the device requirement, a device can be fabricated in a normal fashion (transparent or semitransparent anode on a transparent substrate) or a reversed structure (transparent or semitransparent cathode on a transparent substrate). The mentioned EIJL, ETL, HTL, HIJL as well as the EL host material can be small molecules, oganometallic compounds, oligomers or polymers.

Preparation of these Os(II) complexes can involve the exploitation of recently explored blue-emitting Os complex $[Os(fppz)_2(CO)_2]$ (Wu, P.-C et al. *Organometallics*, 2003, 22, 4938 or its relevant analogue $[Os(fptz)_2(CO)]_2$ as the starting material. Alternatively, for example, see examples 5~14 and Examples 20~22). A desired synthesis was first initiated by the treatment of $Me_3NO$ to eliminate the coordinated CO ligands, followed by addition of phosphine ligands. This synthetic scheme has led to the isolation of red-emitting complexes $[Os(fppz)_2L_2]$, L=$PPh_2Me$ (Os1) and L=$PPhMe_2$ (Os2), or $[Os(fptz)_2L_2]$, L=$PPh_2Me$ (Os3) in moderate yields (40-72%). These Os metal complexes were fully characterized using spectroscopic methods, while complex Os1 was further examined by the single crystal X-ray diffraction analysis.

Figure 10:
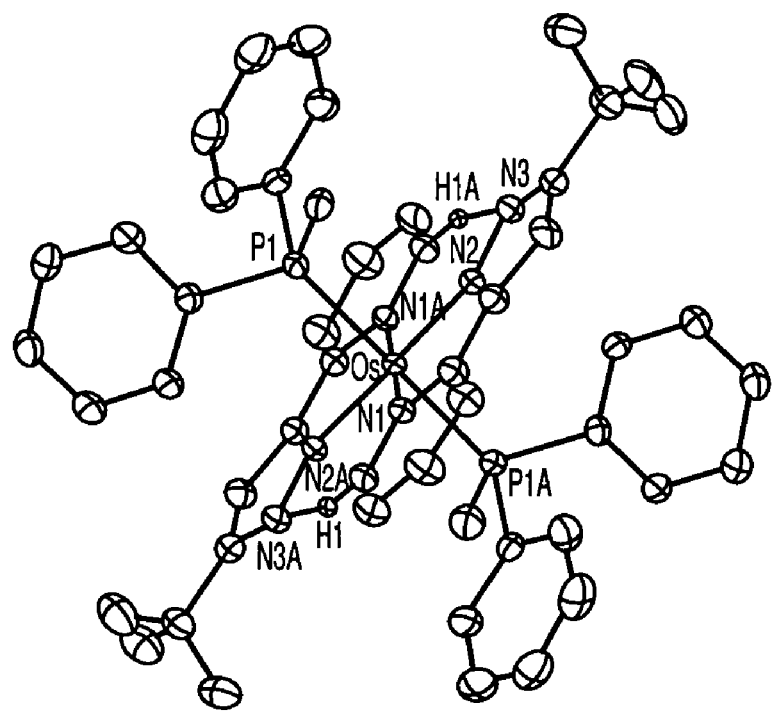
FIG. 10 is an ORTEP diagram of Os1.

As depicted in FIG. 10, the Os atom of complex Os1 is located at the crystallographic center of inversion. The molecular frame reveals an octahedral configuration where two chelating fppz ligands establish a nearly planar $OsN_4$ basal arrangement, together with two $PPh_2Me$ ligands located at the axial dispositions. The planar ligand arrangement is analogous to those of the prophinato ligand in metalloprophyrins such as [Os(TTP)(PPh$_3$)$_2$], TTP=meso-tetraphenyl-prophinate, and [Os(TPP)(CO)(lm)], lm=1-methylimidazole. The measured Os-N$_{(pz)}$ distances of 2.073(2) Å in Os1 are slightly shorter than the respect Os-N$_{(py)}$ bonds of 2.090 (2) Å; both lengths fall in the range expected for a typical N→Os(II) dative bond. Of particular interest is the relatively weak non-bonding contacts (N3A . . . C1=3.305 Å and N3A . . . H1~2.50 Å) observed between the ortho-hydrogen atom of the pyridyl moiety and the N atom of the nearby pyrazolate fragment. In good agreement with this observation, the $^1$H NMR spectrum revealed a significantly downfield signal at δ 10.40, giving an additional indication of the deshielding effect exerted by the N atom. It is speculated that this H-bonding, to a certain extent, is akin to that observed in the cobaloxime complexes.

The absorption and luminescence spectra of complexes Os1-Os3 in CH$_2$Cl$_2$ are shown in FIG. 11. The strong absorption bands at the UV region are assigned to the spin-allowed $^1$π-π* transition of the fppz (or fptz) ligands, owing to their spectral similarity to the free fppz (or fptz) anion. The next lower energy absorption can be ascribed to a typical spin-allowed metal to ligand charge transfer ($^1$MLCT) transition, while two absorption bands extending into the visible region are associated with the spin-orbit coupling enhanced $^3$ ππ* and $^3$MLCT transition. Further luminescence properties (vide infra) support $^3$MLCT to be in the lowest triplet state with peak wavelengths at 542 (ϵ=1300), 553 (ϵ=1600) and 560 nm (ϵ=950 M$^{-1}$ cm$^{-1}$) for complexes Os1, Os2 and Os3, respectively. It is notable that substitution with strong electron donors such as PPh$_2$Me and PPhMe$_2$ ligands not only increase the entire transition dipole moment, but also cause a significant red-shift due to the enhancement of dative interaction with Os(II), and hence raise the d-orbital energy level of the Os metal center. A similar mechanism has been proposed to delineate their electron donating effect for the Os(II) polypyridyl complexes.

Highly intensive luminescence was observed for Os1-Os3 with λ$_{max}$ located at 617, 631 and 648 nm, respectively. The entire emission band originating from a triplet state manifold was ascertained by the O$_2$ quenching rate constant of ~2.1× 10$^9$ M$^{-1}$s$^{-1}$ for Os1-Os3 in CH$_2$Cl$_2$. The significant overlap of the 0-0 onsets between emission and the lowest energy absorption band, in combination with a broad, structureless spectral feature, leads us to conclude that the phosphorescence originates primarily from the $^3$MLCT state. In comparison to Os2 coordinated with PPhMe$_2$ ligand, complex Os1 bearing the PPh$_2$Me group reveals a ~15 nm hypsochromic shift in λ$_{max}$ and can qualitatively be rationalized by a decrease of Os(II) d-orbital energy level due to a stronger electron withdrawing strength of an additional phenyl substitution. Table 1 lists the corresponding photophysical data for the studied complexes in both solution and solid phases. The observed lifetimes of ca. 0.6-0.9 μs in degassed CH$_2$Cl$_2$ are considerably shorter than that of most reported red emitting Ir(III) complexes. In the solid state, the emission maximum for these osmium phosphors shifts to the red possibly due to molecular packing, and the lifetime falls within the range of 0.4-0.6 μs (Table 1). The emission quantum efficiency of Os1-Os3 lies within the range 0.19-0.50 in CH$_2$Cl$_2$ and 0.1-0.3 in the solid state. The results correlate well with unusually large extinction coefficients measured for the $^3$MLCT bands and thus are very desirable for OLED related applications.

Figure 5A:
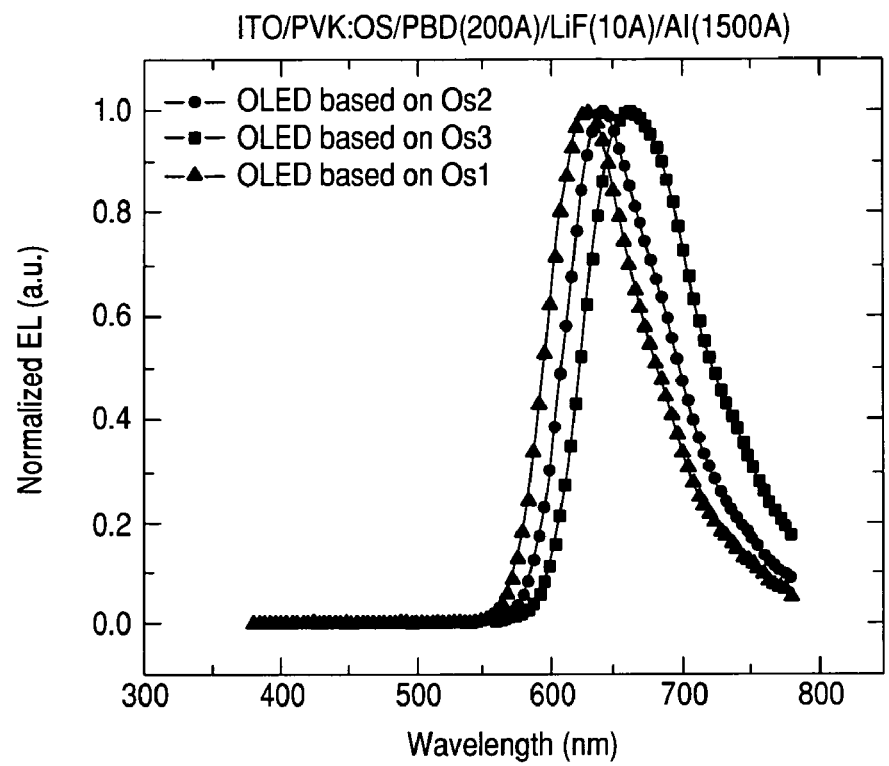
FIG. 5 is a series of graphical depictions of the electroluminescence spectra, the current-voltage and luminescence-voltage, efficiency-voltage characteristics of the embodiment of FIG. 4.
Figure 5B:
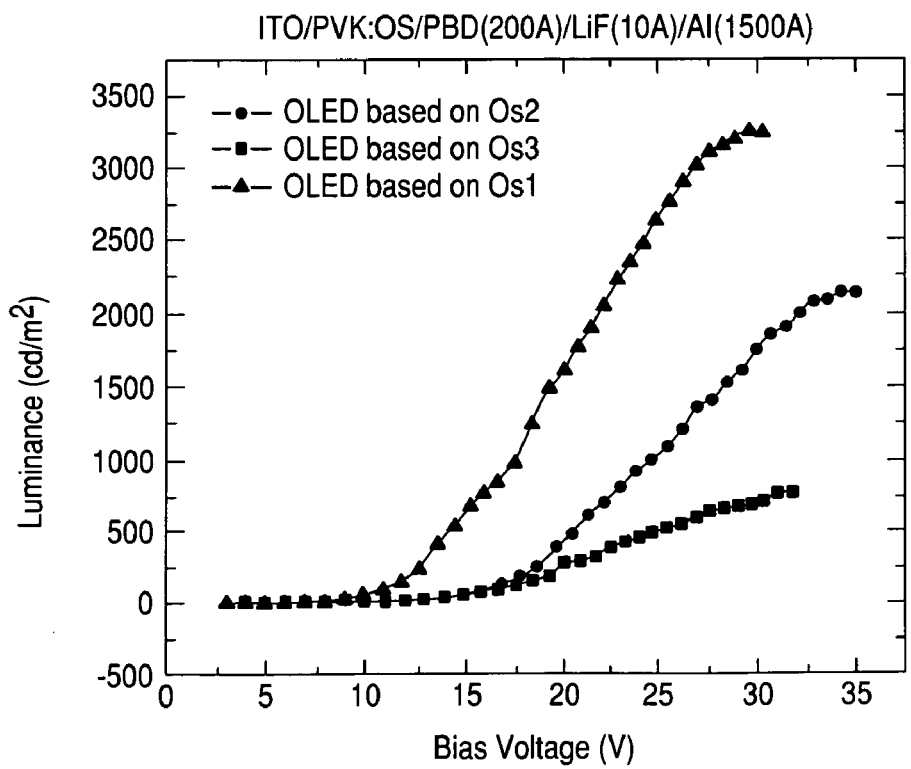
Figure 5C:
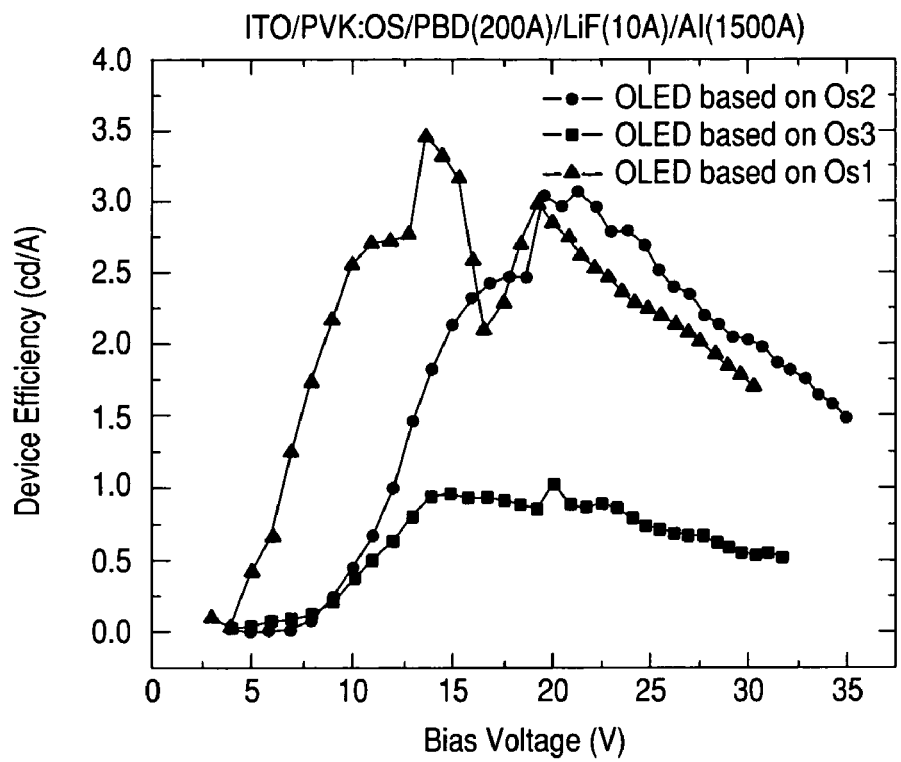
Figure 5D:
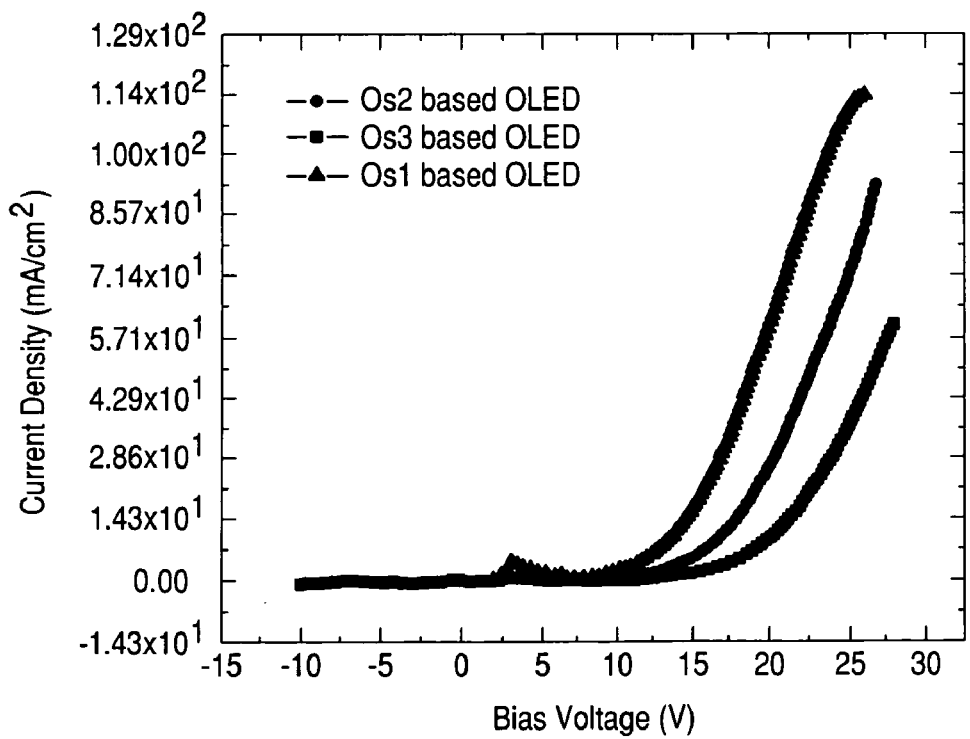

The electroluminescence (EL) spectra of OLEDs based on Os1~Os3 are shown in FIG. 5a. The energy transfer from host material PVK to the Os(II) emitters is very efficient, as supported by the lack of PVK emission in the EL spectra. The EL spectra remained unchanged over a wide rage of bias voltages. The OLEDs with Os1 reached maximum efficiency (η$_{max}$) of 4.0 cd/A at a driving voltage of 13 V with a luminance of 412 cd/m$^2$. The η$_{max}$ of Os2 reached 3.0 cd/A at 21 V with a luminance of 615 cd/m$^2$, while those of Os3 were 1.0 cd/A at 20 V and 271 cd/m$^2$. Although η$_{max}$ and maximum luminance of Os3 appeared to be lower (Table 1), quantum efficiencies and optical power output of these three compounds are similar, considering the fact that the normalized photopic vision functions V(λ) at 630, 640, and 660 nm are 0.265, 0.175 and 0.061 respectively. We believe that the turn-on voltages can be significantly reduced by using either a host material with better charge carrier transport properties or a lower work-function cathode, such as Ca or Mg:Ag alloy.

Thus, in one aspect the invention provides the synthesis of highly efficient red-emitting Os(II) complexes. In contrast to most Os(II) emitters with ionic character, in which the hole and electron injection may be strongly coupled with respect to the counter ions, this new series of complexes are discrete neutral molecules, and thus the anionic fppz (or fptz) ligands are securely attached to the Os(II) center. This unique property may contribute to a more efficient energy transfer and carrier trapping, rendering advantages to the overall device efficiency for Os1~Os3 described above.

Example 19

General Methods

Reactions were performed under nitrogen. Solvents were distilled from appropriate drying agent prior to use. Commercially available reagents were used without further purification unless otherwise stated. Reactions were monitored by TLC with Merck pre-coated glass plates (0.20 mm with fluorescent indicator UV$_{254}$). Compounds were visualized with UV light irradiation at 254 nm and 365 nm. Flash column chromatography was carried out using silica gel from Merck (230-400 mesh). Mass spectra were obtained on a JEOL SX-102A instrument operating in electron impact (EI) mode or fast atom bombardment (FAB) mode. $^1$H and $^{13}$C NMR spectra were recorded on Varian Mercury-400 or INOVA-500 instruments; chemical shifts are quoted with respect to the internal standard tetramethylsilane for $^1$H and $^{13}$C NMR data.

Spectroscopic and Dynamic Measurements: Steady-state absorption and emission spectra were recorded by a Hitachi (U-3310) spectrophotometer and an Edinburgh (FS920) fluorimeter, respectively. Both wavelength-dependent excitation and emission response of the fluorimeter have been calibrated. A configuration of front-face excitation was used to measure the emission of the solid sample, in which the cell was made by assembling two edge-polished quartz plates with various Teflon spacers. A combination of appropriate filters was used to avoid the interference from the scattering light.

Lifetime studies were performed by an Edinburgh FL 900 photon-counting system with a hydrogen-filled/or a nitrogen lamp as the excitation source. Data were analyzed using the nonlinear least squares procedure in combination with an iterative convolution method. The emission decays were analyzed by the sum of exponential functions, which allows partial removal of the instrument time broadening and consequently renders a temporal resolution of ~200 ps.

Quinine sulfate/1.0 $NH_2SO_4$ was used as a reference, assuming a yield of 0.564 with 360 nm excitation, to determined fluorescence quantum yields of the studied compounds in solution. Solution samples were degassed by three freeze-pump-thaw cycles under the vigorous stirring condition. An integrated sphere was applied to measure the quantum yield in the solid state, in which the solid sample film was prepared via the spin-coating method and was excited by a 457 nm $Ar^+$ laser line. The resulting luminescence was acquired by an intensified charge-coupled detector.

Example 20

Alternative preparation of $[Os(fppz)_2(PPh_2Me)_2]$ (Os1) (as Depicted in this Example)

A freshly sublimed $Me_3NO$ (90 mg, 1.19 mmol) was first dissolved into an acetonitrile (5 mL) and the resulting solution was added dropwise to a stirred suspension of $[Os(fppz)_2(CO)_2]$ (200 mg, 0.25 mmol) in toluene (30 mL), giving a clear, yellow orange solution after stirring for 2 minutes at room temperature. After then, the phosphine ligand $PPh_2Me$ (567 µL, 3.0 mmol) was added and the mixture was brought to reflux for 3 hr, during which time the color was found to change to bright red. The reaction was then stopped, toluene solvent and excess of phosphine ligand were removed under vacuum, the solid residue dissolved in 50 mL of ethyl acetate and washed with distilled water (30 mL×2) to remove the remaining $Me_3NO$. The organic phase was dried over $Na_2SO_4$ and the solvent was removed in vacuo to yield red-orange crude product. Further purification was conducted by silica gel column chromatography using a 1:1 mixture of ethyl acetate and hexane, followed by recrystallization from $CH_2Cl_2$ and hexane, giving red-orange crystalline solid (180 mg, 0.18 mmol); yield: 72%.

Example 21

Alternative preparation of $[Os(fppz)_2(PPhMe_2)_2]$ (Os2)

The procedure was identical to that depicted in Example 20, using 200 mg of the osmium complex $[Os(fppz)_2(CO)_2]$ (0.25 mmol), 90 mg of freshly sublimed $Me_3NO$ (1.19 mmol) and 425 µL of phosphine ligand $PPhMe_2$ (2.98 mmol) as starting materials. After the reaction was stopped, the content was washed with water, followed by silica gel column chromatography, and recrystallization from hexane solution to afford the dark red crystalline solid (145 mg, 0.18 mmol) in 55% yield.

Example 22

Alternative Preparation of $[Os(fptz)(PPh_2Me)_2]$ (Os3)

The procedure was identical to that depicted in Example 20, a freshly sublimed $Me_3NO$ (70 mg, 0.92 mmol) was first dissolved into an acetonitrile (5 mL) and the resulting solution was added dropwise to a stirred suspension of $[Os(fptz)_2(CO)_2]$ (200 mg, 0.31 mmol) in toluene (30 mL), giving a clear, yellow orange solution after stirring for 2 minutes at 0° C. After then, the phosphine ligand $PPh_2Me$ (575 µL, 3.10 mmol) was added and the mixture was brought to reflux for 3 hr, during which time the color was found to change to dark red. The reaction was then stopped, toluene solvent and excess of phosphine ligand were removed under vacuum, the solid residue dissolved in 50 mL of ethyl acetate and washed with distilled water (30 mL×2) to remove the remaining $Me_3NO$. The organic phase was dried over $Na_2SO_4$ and the solvent was removed in vacuo to yield dark red crude product. Further purification was conducted by silica gel column chromatography using a 2:1 mixture of ethyl acetate and hexane, followed by recrystallization from acetone and hexane, giving deep red crystalline solid (123 mg, 0.12 mmol); yield: 40%.

Example 23

X-ray Structural Analysis

Single crystal X-ray diffraction data of Os1 from Example 20 were measured on a Bruker SMART CCD diffractometer using Mo—$K_\alpha$ radiation ($\lambda$=0.71073 Å). The data collection was executed using the SMART program. Cell refinement and data reduction were made with the SAINT program. The structure was determined using the SHELXTL/PC program and refined using full-matrix least squares. All non-hydrogen atoms were refined anisotropically, whereas hydrogen atoms were placed at the calculated positions and included in the final stage of refinements with fixed parameters.

Selected crystal data of Os1: $C_{44}H_{36}F_6N_6OsP_2$, M=1014.93, triclinic, space group P −1, a=10.4469 (5), b=10.5233 (6), c=10.6829 (6) Å, $\alpha$=71.968 (1), $\beta$=62.053 (1), $\gamma$=82.167 (1)°, V=986.46 (9) Å$^3$, Z=1, $\rho_{calcd}$=1.708 gcm$^{-1}$, F(000)=502, crystal size=0.35×0.30×0.25 mm, $\lambda$(Mo—$K_\alpha$)= 0.7107 Å, T=295 K, µ=3.383 mm$^{-1}$, 4516 reflections collected ($R_{int}$=0.0253), final $R_1$[I/>2$\sigma$(I)]=0.0182 and w$R_2$(all data)=0.0438.

Example 24

Synthesis of $[Ru(fppz)_2(CO)_2]$

3-Trifluoromethyl-5-(2-pyridyl)pyrazole (pypz)H (620 mg, 2.91 mmol), $Ru_3(CO)_{12}$ (300 mg, 0.47 mmol) and hexane solvent (50 mL) were added to a 160 mL of stainless steel autoclave. The autoclave was sealed and slowly brought up to 185° C. for 36 hours. After that, the autoclave was cooled, the solvent was evaporated to dryness, and the solid residue was purified by column chromatography on $SiO_2$, eluting with a 1:1 mixture of ethyl acetate and hexane. Removal of excess solvent produced a light yellow solid, which was purified by sublimation (150 mtorr/165° C.), followed by crystallization from a mixture of $CH_2Cl_2$/hexane, giving the ruthenium complex [Ru(fppz)$_2$(CO)$_2$] as colorless rectangular crystals (191 mg, 0.33 mmol, 70%).

Spectral data: MS (EI, 70 eV), observed m/z (actual) [assignment] {relative intensity}: 582 (582) [M$^+$] {2.88}, 526 (526) [M$^+$–2CO] {12.5}. IR(CH$_2$Cl$_2$): ν(CO), 2076 (s), 2017 (s) cm$^{-1}$. $^1$H NMR (500 MHz, d$_6$-acetone, 294K): δ 8.07~8.03 (m, 4H, H$_{py}$) 7.38 (d, J$_{HH}$=1 Hz, 2H, H$_{pz}$), 7.32 (ddd, J$_{HH}$=6 Hz, 6 Hz and 3 Hz, 2H, H$_{py}$) 7.09 (dd, J$_{HH}$=6 Hz and 1 Hz, 2H, H$_{py}$). $^{13}$C NMR (125 MHz, d$_6$-acetone, 294K): δ 194.7 (CO), 154.4 (C$_{py}$), 150.7 (C$_{pz}$), 148.9 (CH$_{py}$), 146.7 (q, $^2$J$_{CF}$=36.6 Hz, C$_{pz}$), 141.7 (CN$_{py}$), 124.5 (CH$_{pz}$), 123.1 (q, $^1$J$_{CF}$=266.3 Hz, CF$_3$), 121.7 (CH$_{py}$), 104.3 (CH$_{py}$). $^{19}$F NMR (470 MHz, d$_6$-acetone, 294K): δ –60.2 (s). Anal. Calcd. for $C_{20}H_{10}F_6N_6O_2Ru$: C, 41.372; N, 14.68; H, 1.85. Found: C, 41.32; N, 14.46; H, 1.73.

Example 25

Synthesis of [Ru(ifpz)$_2$(PPh$_2$Me)$_2$]

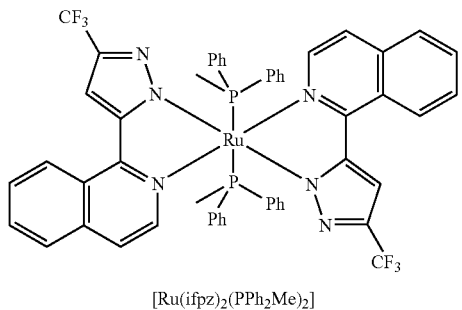

[Ru(ifpz)2(PPh2Me)2]

A 50 mL reaction flask was charged with 3-trifluoromethyl-5-(1-isoquinolyl)pyrazole (ifpz)H, 390 mg, 1.94 mmol), Ru$_3$(CO)$_{12}$ (200 mg, 0.31 mmol), and 20 mL of anhydrous diethylene glycol monoethyl ether (DGME). The mixture was heated at 160~170° C. for 24 hours. The temperature was then lowered to ~120° C., freshly sublimed Me$_3$NO (85 mg, 1.53 mmol) dissolved in 12 mL of DGME was added, and stirring was continued for 5 min. Finally, PPh$_2$Me (840 μL, 4.50 mmol) was injected into the mixture. In the meantime, the temperature of the solution was raised to 180° C. After 24 hours, the reaction was stopped. The solvent was evaporated under vacuum, and the residue was washed with distilled water (20 mL×2). Recrystallization was achieved by a slow diffusion of hexane vapor into a saturated ethyl acetate solution at room temperature, giving orange crystalline solids (550 mg, 0.61 mmol) in 65% yield.

Spectral data: MS (FAB, $^{102}$Ru): m/z 1026 (M$^+$), 826 (M$^+$– PPh$_2$Me), 626 (M$^+$–2PPh$_2$Me). $^1$H NMR (400 MHz, d$_6$-acetone): δ 10.62 (d, 2H, J$_{HH}$=6.4 Hz), 8.33 (d, 2H, J$_{HH}$=7.6 Hz), 7.85 (d, 2H, J$_{HH}$=7.7 Hz), 7.65 (dd, 2H, J$_{HH}$=6.8, 7.6 Hz), 7.57 (dd, 2H, J$_{HH}$=7.7, 6.8 Hz), 7.52 (d, 2H, J$_{HH}$=6.4 Hz), 7.36 (s, 2H), 6.85~6.80 (m, 8H), 6.77~6.75 (m, 4H), 6.69~6.63 (m, 8H), 1.82 (t, 6H, J$_{HP}$=3.0 Hz, Me). $^{19}$F NMR (470 MHz, d$_6$-acetone): δ –59.1 (s, CF$_3$). $^{31}$P NMR (202 MHz, d$_6$-acetone): δ 15.7 (s). Anal. Calcd for $C_{52}H_{40}F_6N_6P_2Ru$: C, 60.88; N, 8.19; H, 3.93. Found: C, 60.88; N, 8.10; H, 4.04.

Example 26

Synthesis of [Ru(ibpz)$_2$(dppe)]

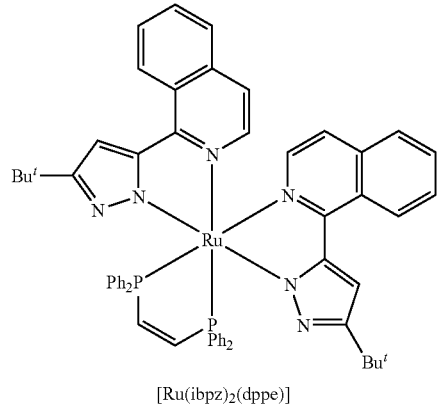

[Ru(ibpz)2(dppe)]

To a 50 mL reaction flask was added [Ru(dppe)(CO)$_3$] (757 mg, 1.30 mmol), 3-tert-butyl-5-(1-isoquinolyl)pyrazole (ibpzH, 685 mg, 2.72 mmol), and 20 mL of anhydrous DGME solvent. The mixture was heated at 170~180° C. for a period of 24 hours. After that, the solution was evaporated to dryness and the residue was purified by recrystallization from saturated ethyl acetate solution, giving red crystalline solids (765 mg, 0.77 mmol) in 59% yield.

Spectral data: MS (FAB, $^{102}$Ru): m/z 998 (M$^+$), 747 (M$^+$– ibpz), 498 (M$^+$–2 ibpz). $^1$H NMR (500 MHz, d$_6$-acetone): δ 8.55 (d, 2H, J$_{HH}$=7.5 Hz), 8.06 (t, 4H, J$_{HH}$=9.0 Hz), 7.87~7.75 (m, 2H), 7.62 (d, 2H, J$_{HH}$=7.5 Hz), 7.56 (dt, 2H, J$_{HH}$=8.5, 1.0 Hz), 7.51 (dt, 2H, J$_{HH}$=8.5, 1.0 Hz), 7.30 (t, 2H, J$_{HH}$=7.0 Hz), 7.18 (t, 4H, J$_{HH}$=7.0 Hz), 6.94 (dd, 2H, J$_{HH}$=8.0, 2.0 Hz), 6.91~6.86 (m, 4H), 6.83 (s, 2H), 6.79 (t, 4H, J$_{HH}$=8.0 Hz), 6.66 (t, 4H, J$_{HH}$=7.0 Hz), 1.53 (s, 18H, $^t$Bu). $^{31}$P NMR (202 MHz, d$_6$-acetone): 672.4 (s). Anal. Calcd. for $C_{58}H_{54}N_6P_2Ru$: C, 69.79; N, 8.42; H, 5.45. Found: C, 70.23; N, 8.43; H, 5.39.

Thus, it will be appreciated that there has been provided herein Os(II) compounds having phosphorescent properties, and uses thereof.

TABLE 1

Photochemical properties of Os(II) carbonyl complexes.[a]

| | $\lambda_{max}$ (nm)[b] | $\lambda_{max}^{em}$ (nm) | Φ (%)[c] | τ (μs) |
|---|---|---|---|---|
| Os(fppz)$_2$(CO)$_2$ | 254, 311 | 430, 457, 480 | 14.0 | 18.3 |
| Os(fmpz)$_2$(CO)$_2$ | 254, 306 | 428, 455, 480 | 4.1 | 6.3 |
| Os(fptz)$_2$(CO)$_2$ | 243, 307 | 420, 446, 468 | 23.3 | 2.88 |
| Os(bptz)$_2$(CO)$_2$ | 250, 333 | 455, 480, 507 | 47.1 | 39.9 |

[a]All sample solutions were degassed and the spectra recorded in CH$_3$CN at room temperature.
[b]The dominant absorption band at spectral regions of 225~280 nm, is ascribed to the local $^1$ππ* transition of pyridine and/or triazolate (or pyrazole). The broad, structureless band maximized at 306~333 nm is attributed to a pyrazole or triazolate-to-pyridine intra-ligand ππ* transition, no visible absorption could be resolved in the region of 380~700 nm, suggesting that all MLCT transitions are hidden in the UV region of the strong intra-ligand ππ* transitions.
[c]Quinine sulfate with an emulsion yield of Φ~0.57 in 0l.1M H$_2$SO$_4$ served as the standard to calculate the emission quantum yield. Sample solutions were degassed by three freeze-pump-thaw cycles.

TABLE 2

Photochemical properties of Os(II) phosphine complexes.[a]

| | $\lambda_{max}$ (nm) ($\epsilon$, $M^{-1}cm^{-1}$)[b] | $\lambda_{max}^{em}$ (nm) | $\Phi$ (%)[c] | $\tau$ (ns) |
|---|---|---|---|---|
| $Os(fppz)_2(PPh_2Me)_2$ | 402 (14900), 453 (2600), 535 (1600) | 620 | 43.4 | 831 |
| $Os(fppz)_2(PPhMe_2)_2$ | 408 (14600), 460 (2100), 547 (1400) | 637 | 25.6 | 661 |
| $Os(bppz)_2(PPh_3)_2$ | 408 (10600), 466 (3000), 572 (1300) | 647 | 0.3 | |
| $Os(bppz)_2(PPh_2Me)_2$ | 408 (13600), 467 (3100), 576 (1500) | 666 | 2.5 | 214 |
| $Os(pppz)_2(PPh_3)_2$ | 406 (17500), 450 (3500), 542 (1900) | 650 | 0.1 | |
| $Os(pppz)_2(PPh_2Me)_2$ | 412 (10500), 471 (2400), 575 (1000) | 654 | 0.9 | |
| $Os(fptz)_2(PPh_2Me)_2$ | 403 (15600), 450 (2400), 537 (1400) | 618 | 55.4 | 1021 |
| $Os(fptz)_2(PPhMe_2)_2$ | 408 (16000), 461 (2000), 547 (1400) | 635 | 12.3 | 782 |
| $Os(bptz)_2(PPh_2Me)_2$ | 405 (16800), 467 (2900), 559 (1500) | 650 | 13.3 | 608 |
| $Os(mptz)_2(PPh_2Me)_2$ | 408 (10700), 465 (2500), 580 (1200) | 664 | 2.3 | 218 |
| $Os(hptz)_2(PPh_2Me)_2$ | 401 (15000), 451 (2300), 532 (1400) | 616 | 63.7 | 1094 |
| $Os(hptz)_2(PPhMe_2)_2$ | 407 (20000), 460 (2500), 546 (1700) | 633 | 29.2 | 834 |

[a]All sample solutions were degassed and the spectra recorded in $CH_3CN$ at room temperature.
[b]These absorption bands were due to the $^1\pi\pi^*$, $^1MLCT$ and the combination of $^3\pi\pi^*$ and $^3MLCT$ transitions, respectively.
[c]4-(Dicyanomethylene)-2-methyl-6-(p-dimethylaminostyryl)-4H-pyran (DCM, assuming a yield of 0.44 in methanol) was used as a reference to determined fluorescence quantum yields. Sample solutions were degassed by three freeze-pump-thaw cycles.

TABLE 3

Some electroluminescent characteristics of the embodiment of FIG. 4.

| | V @ 1 $cd/m^2$ (V) | $L_{max}$ ($cd/m^2$) | Max. Efficiency (cd/A) | $\lambda_{max}$ (nm) |
|---|---|---|---|---|
| Os1 | 5.5 | 3300 | ~3.5 | 626 |
| Os2 | 8.5 | 2100 | ~3.0 | 640 |
| Os3 | 8.5 | 775 | ~1.0 | 658 |

TABLE 4

Some electroluminescent characteristics of the embodiment of FIG. 6.

| | V @ 1 $cd/m^2$ (V) | $L_{max}$ ($cd/m^2$) | Max. Efficiency (cd/A) | $\lambda_{max}$ (nm) |
|---|---|---|---|---|
| Os1 | 8.5 | 4500 | ~7.0 | 626 |
| Os2 | 9.0 | 2448 | ~3.5 | 640 |
| Os3 | 9.5 | 1000 | ~1.3 | 658 |

TABLE 5

Photophysical and electrochemical properties of Os1~Os3.

| Complex | $\lambda_{abs}^a$ nm (log $\epsilon$) | $\lambda_{em}^a$ nm | $\Phi^a$ | $\tau^a$ ns | $E_T^b$ eV | $E_{1/2}^{ox}$ mV[c] | $E_{HOMO}$ eV[d] | $E_{LUMO}$ eV[e] |
|---|---|---|---|---|---|---|---|---|
| Os1 | 405 (4.2) 454 (3.4) 542 (3.1) | 620 | 0.5 | 855 | 2.00 | 231 | 4.72 | 2.15 |
| Os2 | 411 (4.2) 456 (3.4) 553 (3.2) | 631 | 0.19 | 725 | 1.97 | 157 | 4.65 | 2.13 |
| Os3 | 406 (4.1) 466 (3.3) 560 (3.0) | 648 | 0.25 | 634 | 1.92 | 176 | 4.67 | 2.18 |

[a]Measured in degassed $CH_2Cl_2$ solutions at room temperature.
[b]The triplet energy was estimated from the phosphorescence peak.
[c]$E_{1/2}^{ox}$ stands for the half-wave oxidation (p-doping) potential vs an Ag quasi-reference.
[d]Estimated from $E_{1/2}^{ox}$ by using an empirical equation $E_{HOMO} = E_{1/2}^{ox} + 4.49$ eV.
[e]Estimated from $E_{HOMO}$ and optical energy gap ($S_0 \rightarrow {}^1MLCT$).

TABLE 6

OLED device performance of Os(II) complexes doped into the PVK host.

| Doping level (wt %) | Turn-on voltage $(V)^a$ | EL peak (nm) | $\eta_{LE}$ at 1.0 $mA/cm^2$ (cd/A) | $\eta_{LE}$ at 100 $mA/cm^2$ (cd/A) | Maxium luminance ($cd/m^2$) |
|---|---|---|---|---|---|
| Os1 | | | | | |
| 1 | 9 | 616 | 2.1 | 1.8 | 2400 (20 V) |
| 5 | 10 | 620 | 2.1 | 1.9 | 2800 (20 V) |
| 10 | 9 | 626 | 6.5 | 3.8 | 4235 (28 V) |
| 15 | 9 | 626 | 1.0 | 1.2 | 2150 (24.5 V) |
| Os2 | | | | | |
| 1 | 8 | 628 | 1.0 | 0.7 | 891 (18 V) |
| 5 | 12 | 636 | 1.1 | 1.0 | 1581 (23.5 V) |
| 10 | 9 | 640 | 2.8 | 2.1 | 2475 (32 V) |
| 15 | 9 | 640 | 0.9 | 0.8 | 1350 (24 V) |

TABLE 6-continued

OLED device performance of Os(II) complexes doped into the PVK host.

| Doping level (wt %) | Turn-on voltage (V)[a] | EL peak (nm) | $\eta_{LE}$ at 1.0 mA/cm² (cd/A) | $\eta_{LE}$ at 100 mA/cm² (cd/A) | Maxium luminance (cd/m²) |
|---|---|---|---|---|---|
| | | Os3 | | | |
| 1 | 9 | 392[b] | 0.6 | 0.3 | 373 (19 V) |
| 5 | 14 | 660 | 0.4 | 0.4 | 845 (25 V) |
| 10 | 9 | 660 | 1.2 | 0.7 | 1000 (31 V) |
| 15 | 10 | 662 | 0.3 | 0.4 | 805 (26 V) |

[a]Voltage required to achieve a luminance of 1 cd/m2.

[b]The EL emission from PVK became dominant in the device with 1.0 wt % Os(II) complex Os3

Scheme 1.
The structures of Os(II) carbonyl complexes depicted in Table 1.

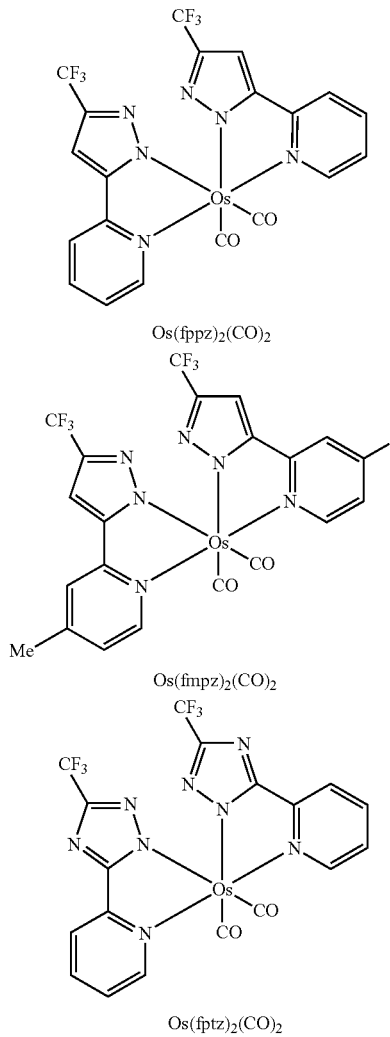

Os(fppz)₂(CO)₂

Os(fmpz)₂(CO)₂

Os(fptz)₂(CO)₂

Scheme 2.
The structures of Os(II) phosphine complexes depicted in Table 2.

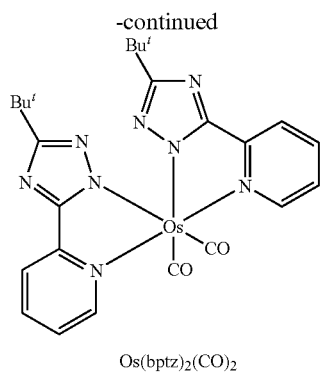

Os(bptz)₂(CO)₂

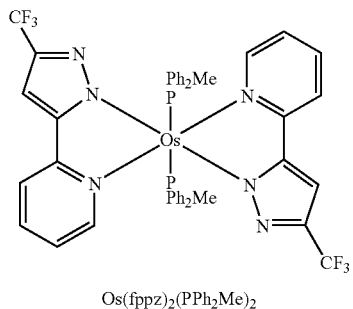

Os(fppz)₂(PPh₂Me)₂

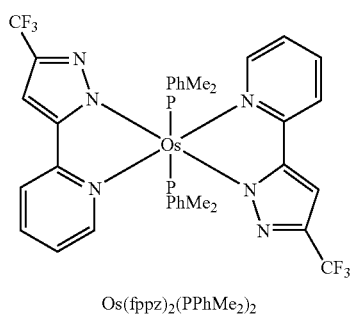

Os(fppz)₂(PPhMe₂)₂

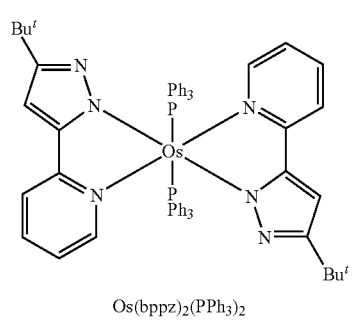

Os(bppz)₂(PPh₃)₂

-continued
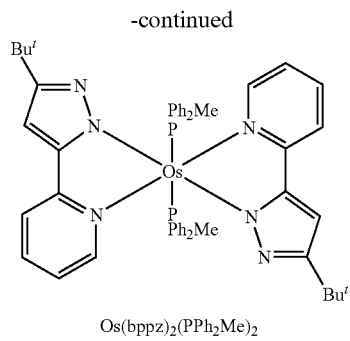
Os(bppz)₂(PPh₂Me)₂
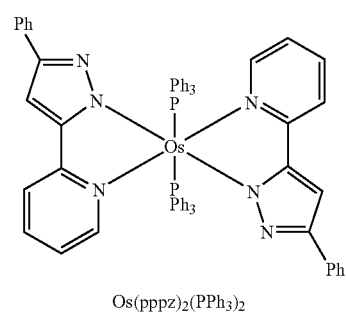
Os(pppz)₂(PPh₃)₂
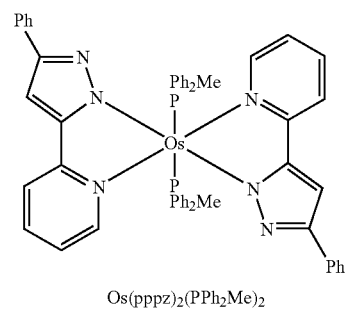
Os(pppz)₂(PPh₂Me)₂
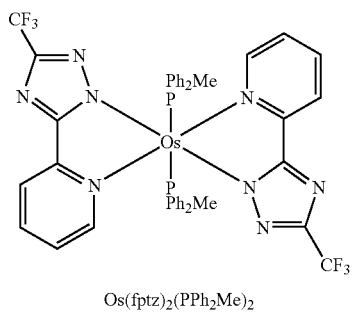
Os(fptz)₂(PPh₂Me)₂
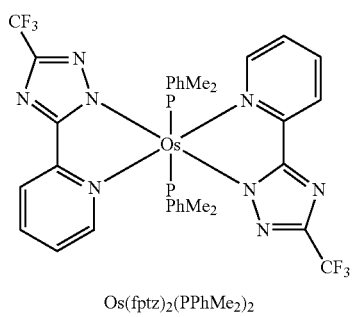
Os(fptz)₂(PPhMe₂)₂
-continued
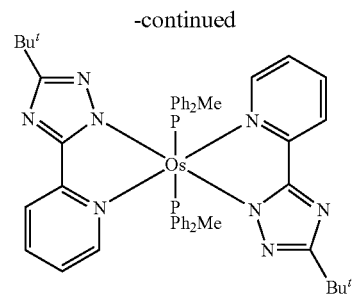
Os(bptz)₂(PPh₂Me)₂
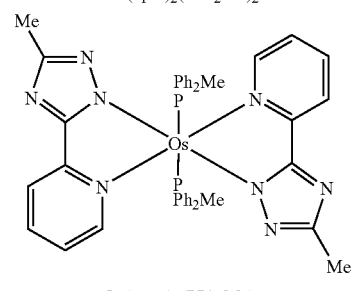
Os(mptz)₂(PPh₂Me)₂
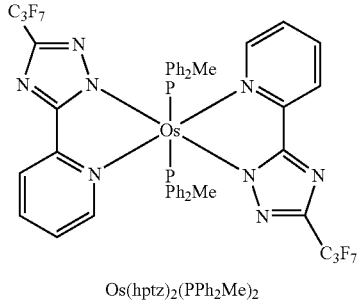
Os(hptz)₂(PPh₂Me)₂
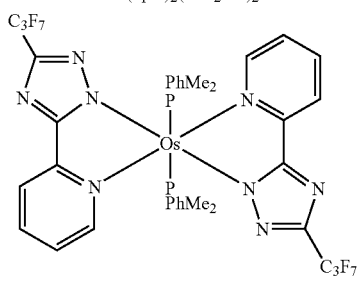
Os(hptz)₂(PPhMe₂)₂
We claim:
1. A compound of structure III:
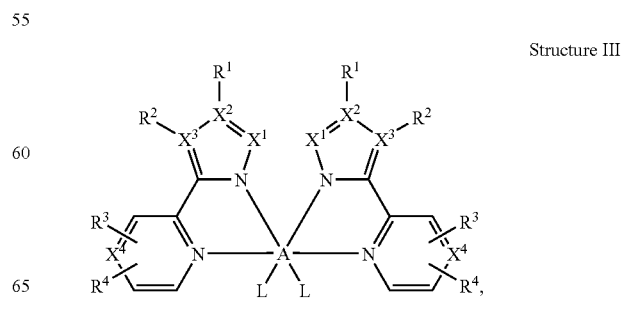
Structure III wherein:
A is Os or Ru;
L stands for a neutral donor ligand other than CO;
L can occupy either cis or trans orientation;
$X^1$, $X^2$ and $X^3$ are independently C or N;
when $X^2$ is N, $R^1$ is omitted;
when $X^3$ is N, $R^2$ is omitted;
$R^1$ is H, C1-C8 alkyl, C1-C8 substituted phenyl or C1-C4 perfluoroalkyl;
$R^2$ is H, F and/or a cyano substituent;
$X^4$ of the hexagonal fragment is either C or N;
$X^4$ may be located at any position of the hexagonal ring other than at the already present N position or the C-atom connecting the hexagonal ring to the pentagonal ring when $X^4$ is N and $R^3$ and $R^4$ are not linked to X4; and
$R^3$ is H, or C1-C3 alkyl;
$R^4$ is H, or C1-C3 alkyl, or;
$R^3$ and $R^4$ together form the additional conjugated unit with structure

2. The compound of claim 1 wherein A is Os.
3. The compound of claim 1 wherein A is Ru.
4. The compound of claim 1 wherein $X^1$ is C.
5. The compound of claim 1 wherein $X^1$ is N.
6. The compound of claim 1 wherein $X^2$ is C.
7. The compound of claim 1 wherein $X^2$ is N.
8. The compound of claim 1 wherein $X^3$ is C.
9. The compound of claim 1 wherein $X^3$ is N.
10. The compound of claim 1 wherein $R^2$ is selected from the group consisting of a fluoro substituent and cyano substituent.
11. A method of making a compound as set forth in claim 2 comprising the steps of initiating a condensation reaction of a bidentate chelating ligand having a general formula selected from the group consisting of

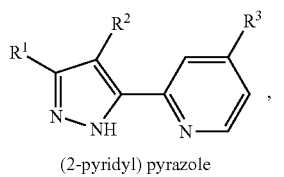
(2-pyridyl) pyrazole

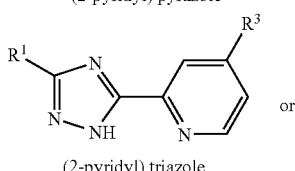
(2-pyridyl) triazole

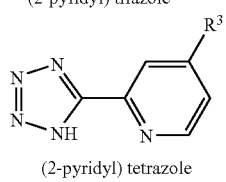
(2-pyridyl) tetrazole together with an osmium metal reagent $Os_3(CO)_{12}$ and in the substantial absence of solvent media or in the presence of a high boiling polar organic solvent at elevated temperature.

12. The compound of claim 2 wherein substituents are selected to provide a structure selected from the group consisting of 3a, 3b, or 3c;

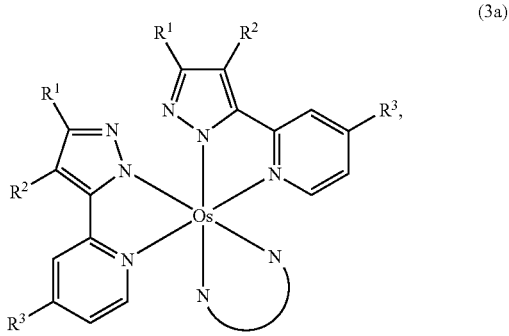
(3a)

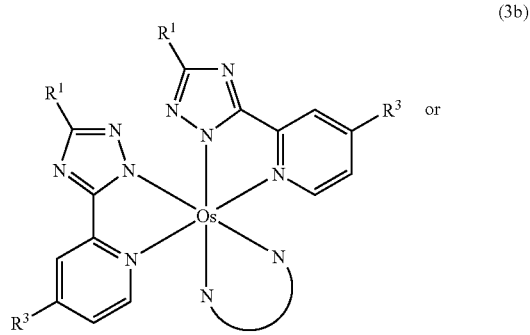
(3b)

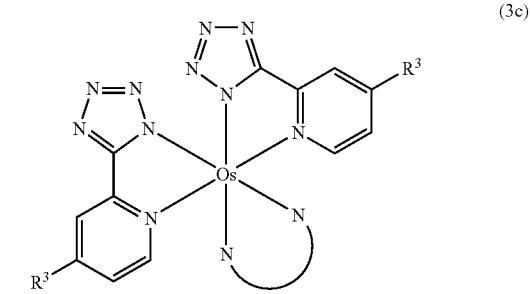
(3c)

wherein N^N are chelate ligands selected from the group consisting of ethylene diamine, tetramethylethylene diamine, 2, 2'-bipyridine, 1,10-phenanthroline, 2-(2'-pyridyl) benzoxazole and their alkyl or aryl substituted derivatives.

13. The compound of claim 2 wherein substituents are selected to provide a structure selected from the group consisting of 4a, 4b or 4c:

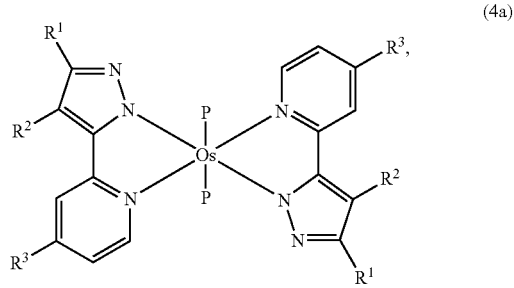
(4a)

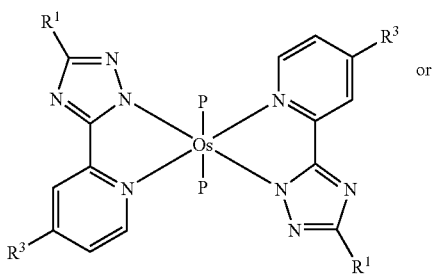

(4b)

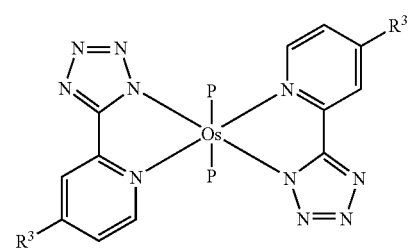

(4c)

wherein P is a donor ligand selected from phosphine, phosphate and arsenine and wherein the phosphine donor ligand is selected from the group consisting of $PPh_3$, $PPh_2Me$, $PPhMe_2$, $PMe_3$, $PPh_2(C_2F_5)$, $PPh(C_2F_5)_2$, $PPh_2Et$, $PPhEt_2$, $PEt_3$, $PPh_2(CH=CH_2)$ and $PPh(CH=CH_2)_2$, and the phosphite ligand is selected from the group consisting of $P(OPh)_3$, $P(OMe)_3$ and $P(OEt)_3$ and the arsine ligand is selected from the group consisting of $AsPh_3$ and $AsMe_3$.

14. A method of making a compound of claim 13 comprising initiating a condensation reaction of a bidentate chelating ligand having a general formula selected from the group consisting of;

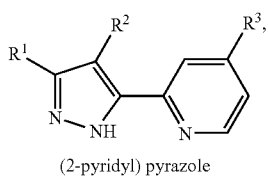

(2-pyridyl) pyrazole

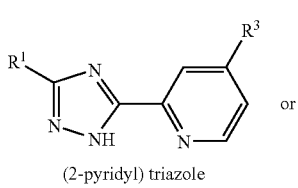

(2-pyridyl) triazole

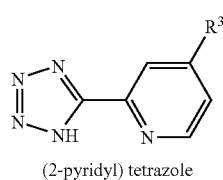

(2-pyridyl) tetrazole together with an osmium carbonyl reagent $Os_3(CO)_{12}$ and in the presence of a high boiling polar organic solvent at elevated temperature, followed by treatment of the resulting reaction mixture with a freshly sublimed decarbonylation reagent $Me_3NO$ or $Et_3NO$, and the phosphine donor ligand.

15. The compound of claim 2 wherein substituents are selected to provide structures selected from the group consisting of 5a, 5b or 5c:

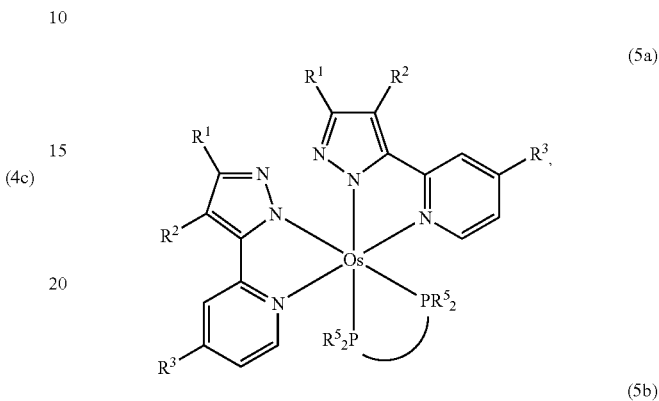

(5a)

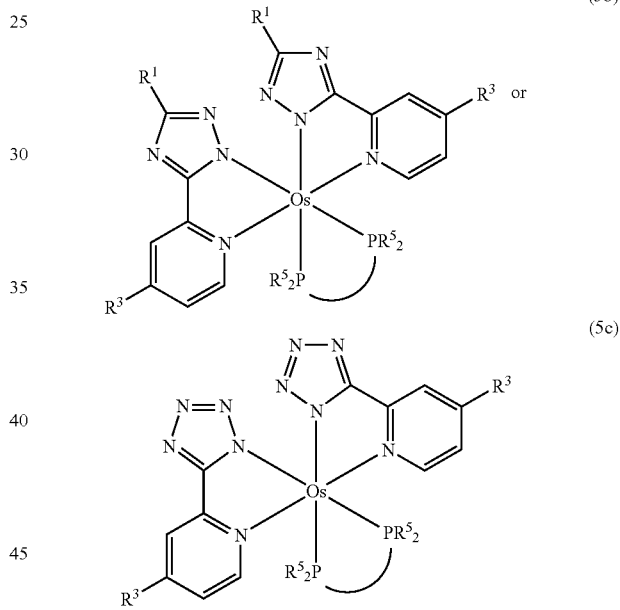

(5b)

(5c)

wherein the chelating diphosphine ligand $R^5_2P\hat{\ }PR^5_2$ is selected from the group consisting of 1,2bis(dimethylphosphino)ethane, 1,2-bis(diphenylphosphino)ethane, 1,2-bis(diphenylphosphino)benzene, 1,2-bis(diethoxylphosphino)benzene, cis-1,2-bis(diphenylphosphino)ethylene, bis(dipentafluoroethylphosphino)ethane, 1,2-bis(dipentafluorophenylphosphino)ethane, 1,3-bis(dimethylphosphino)propane, 1,3-bis(diphenylphosphino)propane, 1,4-bis(dimethylphosphino)butane and 1,4-bis(diphenylphosphino)butane, for which the carbon spacer linking the phosphorous donor group is considerably lengthened to increase the chelating bite angle at the Os(II) metal center.

16. The compound of claim 1 and wherein the 2-pyridyl unit of the pyrazolate, triazolate and tetrazolate ligands is further modified to include an aromatic heterocycle molecule to replace the pyrazolate fragment of the anionic ligand with an imidiazolate or an indazolate unit.

17. The compound of claim 16 wherin the aromatic hetercycle molecule is selected from the group consisting of:

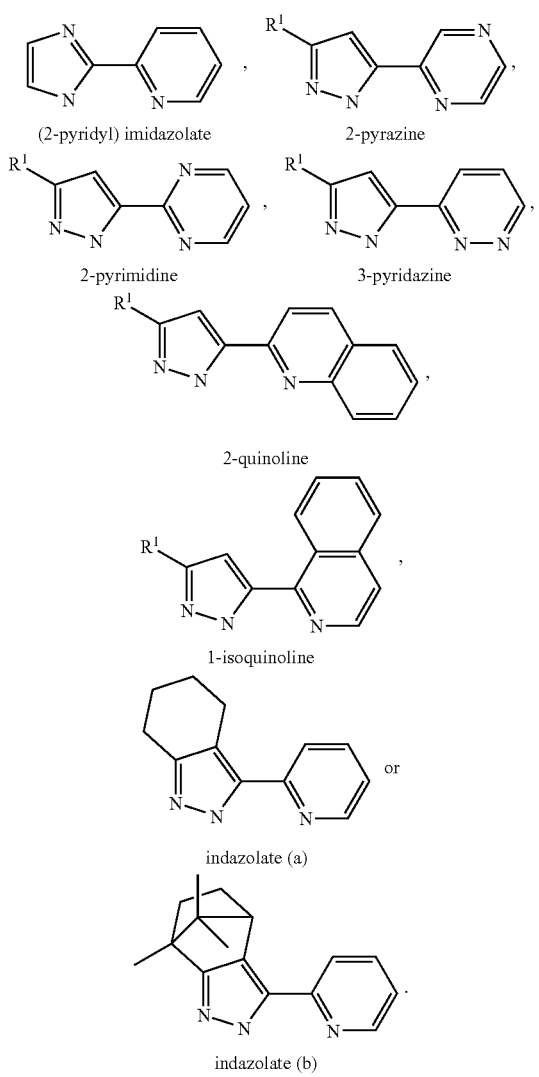

18. The compound of claim 16 wherein the aromatic heterocycle molecule is selected from the group consisting of pyrazine, pyrimidine, pyridazine, quinoline and isoquinoline.

19. A light emitting device comprising a pair of electrodes, a substrate, at least one organic layer on said substrate forming a light emitting structure, said at least one organic layer including as a functional phosphorescent component the compound of structure III as defined in claim 1.

20. The light-emitting device of claim 19 wherein said compound of structure III is disposed in a substantially non-ionic environment.

21. The light-emitting device of claim 19 and wherein said light-emitting diode is at least one of an Organic Light Emitting Diode (OLED), a Polymer Light Emitting Diode (PLED), or said at least one functional layer is formed from small molecules including oligomers and other of said at least one functional layers are formed from polymers or polymer/small molecule composite materials.

22. The device of claim 19 where some of said at least one functional layers can be made of small molecules including oligomers and other of said at least one functional layers can be made of polymers or polymer/small molecule composite materials.

23. The device of claim 19 further including a second phosphorescent material.

24. The light-emitting device of claim 23 wherein the compound of structure III is located in a substantially non-ionic environment.

25. The light-emitting device of claim 23 and further comprising a hole injection promotion layer and at least one hole transport layer, said hole injection promotion layer being adjacent to said at least one hole transport layer.

26. The light-emitting device of claim 23 and further including an electron injection promotion layer and at least one electron transport layer, said electron injection promotion layer being adjacent said at least one electron transport layer.

27. The light-emitting device of claim 25 and further including an electron injection promotion layer, said electron injection promotion layer is LiF.

28. The light-emitting device of claim 25 and wherein said hole injection promotion layer is [Poly (ethylene dioxythiophene: polystryrene sulfonate)] (PEDOTPSS).

29. The light emitting device of claim 19 and wherein said at least one organic layer is deposited by one of a dry deposition method or a wet thin film processing method.

30. The light-emitting device of claim 29 wherein the dry deposition method is selected from the group consisting of thermal deposition and sputtering deposition and PECVD deposition and MOCVD deposition.

31. The light-emitting device of claim 29 and wherein the wet thin film processing method is selected from the group of Langmuir-Blodgett, screen printing, and ink-jet printing, and solution dipping and spin-coating.

32. A light emitting device comprising an anode and a cathode, a hold transport layer and an electron transport layer, and wherein at least one of said hold transport layer and said electron transport layer comprises an active material comprising the compound of structure III as defined in claim 1.

* * * * *